US005744506A

United States Patent [19]
Goldman et al.

[11] Patent Number: 5,744,506
[45] Date of Patent: Apr. 28, 1998

[54] PROCESS FOR MAKING ABSORBENT FORAM MATERIALS FOR AQUEAOUS FLUIDS MADE FROM HIGH INTERNAL PHASE EMULSIONS HAVING VERY HIGH WATER-TO-OIL RATIOS

[75] Inventors: Stephen Allen Goldman, Cincinnati; Michelle Renee Peace, Mason; Paul Seiden, Cincinnati, all of Ohio

[73] Assignee: The Procter & Gamble Company, Cincinnati, Ohio

[21] Appl. No.: 721,648

[22] Filed: Sep. 26, 1996

Related U.S. Application Data

[62] Division of Ser. No. 655,041, May 28, 1996, Pat. No. 5,741,581, which is a division of Ser. No. 563,866, Nov. 29, 1995, Pat. No. 5,650,222, which is a continuation of Ser. No. 370,922, Jan. 10, 1995, abandoned.

[51] Int. Cl.$^6$ ........................................... C08J 9/28
[52] U.S. Cl. ........................... 521/64; 521/62; 521/63
[58] Field of Search .............................. 521/64, 62, 63

[56] References Cited

U.S. PATENT DOCUMENTS

| | | | |
|---|---|---|---|
| 3,255,127 | 6/1966 | Leverkusen et al. | 260/2.5 |
| 3,256,219 | 6/1966 | Will | 260/2.5 |
| 3,431,911 | 3/1969 | Meisel, Jr. | 128/287 |
| 3,563,243 | 2/1971 | Lindquist | 128/287 |
| 3,565,817 | 2/1971 | Lissant | 252/312 |
| 3,640,753 | 2/1972 | Krauch et al. | 117/62.2 |
| 3,734,867 | 5/1973 | Will | 260/2.5 R |
| 3,763,056 | 10/1973 | Will | 260/2.5 L |
| 3,778,390 | 12/1973 | Ulrich, Jr. | 260/2.5 AN |
| 3,806,474 | 4/1974 | Blair | 260/2.5 AG |
| 3,988,508 | 10/1976 | Lissant | 526/344 |
| 3,993,074 | 11/1976 | Murray et al. | 128/286 |
| 3,994,298 | 11/1976 | DesMarais | 128/285 |
| 4,029,100 | 6/1977 | Karami | 128/284 |
| 4,049,592 | 9/1977 | Marans et al. | 260/2.5 AD |
| 4,061,145 | 12/1977 | DesMarais | 128/275 |
| 4,067,832 | 1/1978 | DesMarais | 260/2.5 AB |
| 4,093,570 | 6/1978 | Miyake et al. | 260/2.5 B |
| 4,110,276 | 8/1978 | DesMarais | 521/123 |
| 4,132,839 | 1/1979 | Marans et al. | 521/159 |
| 4,262,052 | 4/1981 | Kannan et al. | 424/306 |
| 4,376,440 | 3/1983 | Whitehead et al. | 604/387 |
| 4,394,930 | 7/1983 | Korpman | 220/444 |
| 4,425,130 | 1/1984 | DesMarais | 604/389 |
| 4,473,611 | 9/1984 | Haq | 428/198 |
| 4,522,953 | 6/1985 | Barby et al. | 521/64 |
| 4,536,521 | 8/1985 | Haq | 521/146 |
| 4,540,717 | 9/1985 | Mahnke et al. | 521/52 |
| 4,554,297 | 11/1985 | Dabi | 521/178 |
| 4,603,069 | 7/1986 | Haq et al. | 428/76 |
| 4,606,958 | 8/1986 | Haq et al. | 428/68 |
| 4,611,014 | 9/1986 | Jones et al. | 521/146 |
| 4,612,334 | 9/1986 | Jones et al. | 521/146 |
| 4,613,543 | 9/1986 | Dabi | 428/304.4 |
| 4,668,709 | 5/1987 | Jones et al. | 521/146 |
| 4,724,242 | 2/1988 | Vassileff | 521/83 |
| 4,725,628 | 2/1988 | Garvey et al. | 521/137 |
| 4,731,391 | 3/1988 | Garvey | 521/137 |
| 4,740,528 | 4/1988 | Garvey et al. | 521/128 |
| 4,775,655 | 10/1988 | Edwards et al. | 502/416 |
| 4,788,225 | 11/1988 | Edwards et al. | 521/147 |
| 4,797,310 | 1/1989 | Barby et al. | 428/71 |
| 4,839,395 | 6/1989 | Masamizu et al. | 521/56 |
| 4,957,810 | 9/1990 | Eleouet et al. | 428/306.6 |
| 4,959,341 | 9/1990 | Wallach | 502/404 |
| 4,961,982 | 10/1990 | Taylor | 428/41 |
| 4,965,289 | 10/1990 | Sherrington et al. | 521/53 |
| 4,966,919 | 10/1990 | Williams, Jr. et al. | 521/54 |
| 4,985,467 | 1/1991 | Kelly et al. | 521/52 |
| 4,985,468 | 1/1991 | Elmes et al. | 521/63 |
| 4,990,541 | 2/1991 | Nielsen et al. | 521/70 |
| 4,992,254 | 2/1991 | Kong | 423/449 |
| 5,021,462 | 6/1991 | Elmes et al. | 521/63 |
| 5,037,859 | 8/1991 | Williams, Jr. et al. | 521/55 |

(List continued on next page.)

FOREIGN PATENT DOCUMENTS

| | | |
|---|---|---|
| 0 017 671 A1 | 10/1980 | European Pat. Off. |
| 0 017 672 A1 | 10/1980 | European Pat. Off. |
| 0 049 768 A1 | 4/1982 | European Pat. Off. |
| 0 299 762 | 1/1989 | European Pat. Off. |
| 0 480 379 A2 | 4/1992 | European Pat. Off. |
| 1340520 | 9/1963 | France . |
| 3 109 929 A1 | 1/1982 | Germany . |
| 2-239863 | 9/1990 | Japan . |
| 2-289608 | 11/1990 | Japan . |
| 3-49759 | 3/1991 | Japan . |
| 1 493 356 | 11/1977 | United Kingdom . |
| 2 078 527 | 1/1982 | United Kingdom . |
| 2 188 055 | 9/1987 | United Kingdom . |
| WO 94/28839 | 12/1994 | WIPO . |

OTHER PUBLICATIONS

A Study of Medium and High Internal Phase Ratio Water/Polymer Emulsions, Lissant, pp. 201–108, 1973.
The Geometry of High–Internal–Phase Ratio Emulsions, Lissant, pp. 462–468 1966.
Low Density, Microcellular polystyrene foams, Aubert and Clough, pp., 2047–2054, 1985.
Mechanical Structure Property Relationships of Microcellulsr, Low Density Foams, LeMay, pp. 21–26, 1991.
New Melamine–based elastic foam, Weber and Kruckau, pp. 843–848, 1985.
Preparation of multishell ICF target plastic foam cushion materials by thermally induced phase inversion processes, Young, Moreno and Marsters, pp. 1094–2004, 1981.

Primary Examiner—Morton Foelak
Attorney, Agent, or Firm—Eric W. Guttag; Carl J. Roof; E. Kelly Linman

[57] ABSTRACT

Low density collapsed absorbent foams materials that, upon contact with aqueous fluids, in particular urine, can expand and absorb these fluids. These low density foams typically have an expanded thickness from about 6 to about 10 times the thickness of the foams in their collapsed state. These low density foams are made by polymerizing high internal phase emulsions (HIPEs) where the volume to weight ratio of the water phase to the oil phase is in the range of from about 55:1 to about 100:1.

10 Claims, 5 Drawing Sheets

U.S. PATENT DOCUMENTS

| | | | |
|---|---|---|---|
| 5,047,225 | 9/1991 | Kong | 423/447.2 |
| 5,065,752 | 11/1991 | Sessions et al. | 128/156 |
| 5,066,684 | 11/1991 | LeMay | 521/64 |
| 5,066,784 | 11/1991 | Sherrington et al. | 530/334 |
| 5,110,838 | 5/1992 | Tokiwa et al. | 521/81 |
| 5,116,880 | 5/1992 | Tokiwa et al. | 521/134 |
| 5,116,883 | 5/1992 | LeMay | 521/178 |
| 5,128,382 | 7/1992 | Elliott, Jr. et al. | 521/178 |
| 5,134,007 | 7/1992 | Reising et al. | 428/78 |
| 5,134,171 | 7/1992 | Hammel et al. | 521/98 |
| 5,147,345 | 9/1992 | Young et al. | 604/378 |
| 5,149,720 | 9/1992 | DesMarais et al. | 521/63 |
| 5,189,070 | 2/1993 | Brownscombe et al. | 521/64 |
| 5,198,472 | 3/1993 | DesMarais et al. | 521/63 |
| 5,200,433 | 4/1993 | Beshouri | 521/64 |
| 5,210,104 | 5/1993 | Bass et al. | 521/64 |
| 5,210,108 | 5/1993 | Spinu et al. | 521/182 |
| 5,221,726 | 6/1993 | Dabi et al. | 528/93 |
| 5,250,576 | 10/1993 | DesMarais et al. | 521/63 |
| 5,252,619 | 10/1993 | Brownscombe et al. | 521/64 |
| 5,260,345 | 11/1993 | DesMarais et al. | 521/148 |
| 5,268,224 | 12/1993 | DesMarais et al. | 428/286 |
| 5,290,820 | 3/1994 | Brownscombe et al. | 521/64 |
| 5,318,554 | 6/1994 | Young et al. | 604/378 |
| 5,331,015 | 7/1994 | DesMarais et al. | 521/62 |
| 5,336,208 | 8/1994 | Rosenbluth et al. | 604/329 |
| 5,336,695 | 8/1994 | Nass et al. | 521/109.1 |
| 5,352,711 | 10/1994 | DesMarais | 521/149 |
| 5,387,207 | 2/1995 | Dyer et al. | 604/369 |

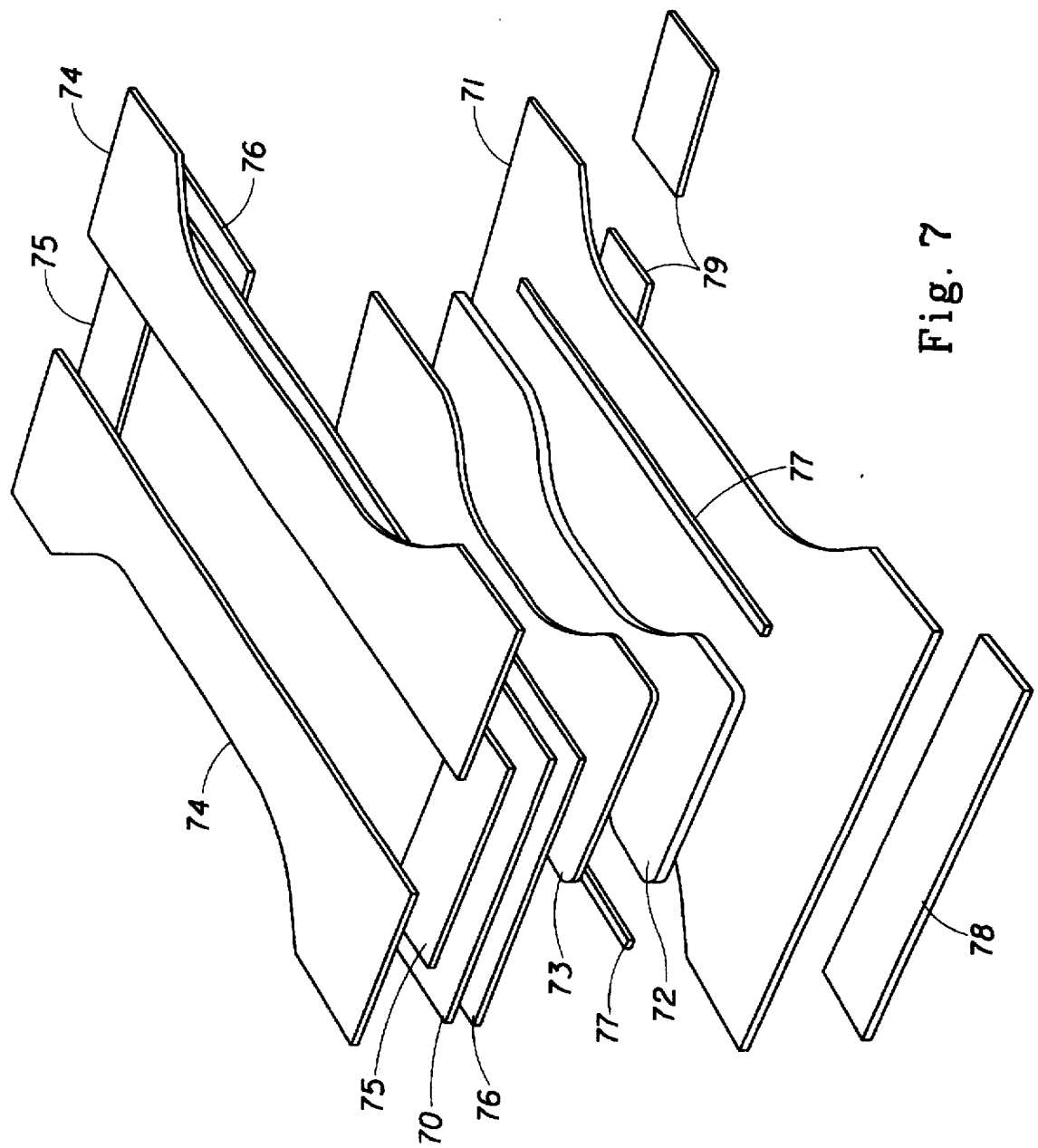

PROCESS FOR MAKING ABSORBENT FOAM MATERIALS FOR AQUEAOUS FLUIDS MADE FROM HIGH INTERNAL PHASE EMULSIONS HAVING VERY HIGH WATER-TO-OIL RATIOS

This application is a division of Ser. No. 08/655,041 filed May 28, 1996, now U.S. Pat. No. 5,741,581, which is a division of Ser. No. 08/563,866 filed Nov. 29, 1995, now U.S. Pat. No. 5,650,222, which is a continuation of Ser. No. 08/370,922 filed Jan. 10, 1995, now abandoned.

FIELD OF THE INVENTION

This application relates to flexible, microporous, open-celled polymeric foam materials having fluid absorption and retention characteristics that make them particularly suitable for absorbing aqueous fluids, e.g., urine. This application particularly relates to absorbent foam materials made from high internal phase emulsions having very high water-to-oil ratios.

BACKGROUND OF THE INVENTION

The development of highly absorbent articles for use as disposable diapers, adult incontinence pads and briefs, and sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging and reduced weight also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain particulate absorbent polymers often referred to as "hydrogels," "superabsorbents" or "hydrocolloid" materials has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such particulate absorbent polymers in absorbent articles. Indeed, the development of thinner diapers has been the direct consequence of thinner absorbent cores that take advantage of the ability of these particulate absorbent polymers to absorb large quantities of discharged aqueous body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and particulate absorbent polymers useful in fashioning thin, compact, nonbulky diapers.

These particulate absorbent polymers were previously unsurpassed in their ability to retain large volumes of fluids, such as urine. A representative example of such particulate absorbent polymers are lightly crosslinked polyacrylates. Like many of the other absorbent polymers, these lightly crosslinked polyacrylates comprise a multiplicity of anionic (charged) carboxy groups attached to the polymer backbone. It is these charged carboxy groups that enable the polymer to absorb aqueous body fluids as the result of osmotic forces.

Absorbency based on capillary forces is also important in many absorbent articles, including diapers. Capillary forces are notable in various everyday phenomena, as exemplified by a paper towel soaking up spilled liquids. Capillary absorbents can offer superior performance in terms of the rate of fluid acquisition and wicking, i.e., the ability to move aqueous fluid away from the point of initial contact. Indeed, the dual-layer core absorbent structures noted above use the fibrous matrix as the primary capillary transport vehicle to move the initially acquired aqueous body fluid throughout the absorbent core so that it can be absorbed and retained by the particulate absorbent polymer positioned in layers or zones of the core.

Other absorbent materials capable of providing capillary fluid transport are open-celled polymeric foams. Indeed, certain types of polymeric foams have been used in absorbent articles for the purpose of actually imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,520 (Garvey et al), issued Apr. 26, 1988 (absorbent composite structure such as diapers, feminine care products and the like that contain sponge absorbents made from certain types of super-wicking, crosslinked polyurethane foams).

The use of absorbent foams in absorbent articles such as diapers can be highly desirable. If made appropriately, open-celled hydrophilic polymeric foams can provide features of capillary fluid acquisition, transport and storage required for use in high performance absorbent cores. Absorbent articles containing such foams can possess desirable wet integrity, can provide suitable fit throughout the entire period the article is worn, and can minimize changes in shape during use (e.g., swelling, bunching). In addition, absorbent articles containing such foam structures can be easier to manufacture on a commercial scale. For example, absorbent diaper cores can simply be stamped out of continuous foam sheets and can be designed to have considerably greater integrity and uniformity than absorbent fibrous webs. Many absorbent cores made from such fibrous webs fall apart during use. Such foams can also be molded into any desired shape, or even formed into integral, unitary diapers.

Particularly suitable absorbent foams for absorbent products such as diapers have been made from High Internal Phase Emulsions (hereafter referred to as "HIPEs"). See, for example, U.S. Pat. No. 5,260,345 (DesMarais et al), issued Nov. 9, 1993 and U.S. Pat. No. 5,268,224 (DesMarais et al), issued Dec. 7, 1993. These absorbent HIPE foams provide desirable fluid handling properties, including: (a) relatively good wicking and fluid distribution characteristics to transport the imbibed urine or other body fluid away from the initial impingement zone and into the unused balance of the foam structure to allow for subsequent gushes of fluid to be accommodated; and (b) a relatively high storage capacity with a relatively high fluid capacity under load, i.e., under compressive forces. These HIPE absorbent foams are also sufficiently flexible and soft so as to provide a high degree of comfort to the wearer of the absorbent article, and can be made relatively thin until subsequently wetted by the absorbed body fluid.

An important issue in making absorbent HIPE foams commercially attractive for use in absorbent products such as diapers is economics. The economics of absorbent HIPE foams depend on the amount and cost of the monomers used per unit of fluid absorbed, as well as the cost of converting the monomers to a usable polymeric foam. Making absorbent HIPE foams economically attractive can require using: (1) less total monomer per unit volume of foam: (2) less expensive monomers: (3) a less expensive process for converting these monomers to a usable absorbent HIPE foam; or (4) combinations of these factors. At the same time, the absorbent HIPE foam must satisfy desired characteristics for absorbent capacity and strength under compressive load without sacrificing tear resistance or resilience to an unacceptable degree. The effort to reduce the cost of such absorbent foams, especially in terms of reducing the total amount of monomer used, can make it very difficult to achieve these desired absorbency and mechanical properties.

As previously noted, a thinner absorbent core is usually a requirement for making relatively thin absorbent articles, such as diapers. Providing relatively thin absorbent HIPE foams that rapidly absorb body fluids when wetted can be very challenging. This especially true if the relatively thin HIPE foam is to be made economically, while at the same time satisfying the desired criteria for absorbent capacity, toughness and strength under compressive load. For example, it has been found that when less monomer is used per unit volume, the resulting absorbent HIPE foam can be too weak to function properly.

Accordingly, it would be desirable to be able to make an open-celled absorbent polymeric foam material that: (1) has adequate or preferably superior fluid handling characteristics, including capillary fluid transport capability and total absorbent capacity for discharged body fluids so as to be desirable for use in absorbent articles such as diapers, adult incontinence pads or briefs, sanitary napkins and the like; (2) can be relatively thin and lightweight during normal storage and use until wetted with these body fluids; (3) has sufficient resiliency, toughness and strength under compressive load to rapidly absorb these body fluids; and (4) can be manufactured economically without sacrificing these desired absorbency and mechanical properties to an unacceptable degree.

DISCLOSURE OF THE INVENTION

The present invention relates to collapsible polymeric foam materials that, upon contact with aqueous fluids (in particular aqueous body fluids such as urine), can expand and absorb these fluids. These absorbent polymeric foam materials comprise a hydrophilic, flexible, nonionic polymeric foam structure of interconnected open-cells. This foam structure has:

A) a specific surface area per foam volume of at least about 0.025 m$^2$/cc;

B) at least about 0.1% by weight of a toxicologically acceptable hygroscopic, hydrated salt incorporated therein;

C) in its collapsed state, an expansion pressure of about 30 kPa or less; and

D) a free absorbent capacity of from about 55 to about 100 mL/g;

E) a ratio of expanded to collapsed thickness of at least about 6:1;

F) a resistance to compression deflection of about 40% or less when measured under a confining pressure of 0.74 psi.

The present invention provides very low density absorbent foams. For a given expanded thickness, these lower density foams are thinner in their collapsed state than prior absorbent HIPE foams. These lower density foams more efficiently utilize the available polymer material and ultimately produce less waste than prior absorbent HIPE foams. As a result, the lower density absorbent foams of the present invention provide an economically attractive means for achieving thinner absorbent cores for absorbent articles such as diapers, adult incontinence pads or briefs, sanitary napkins, and the like. This is achieved while retaining desired absorbency and mechanical properties.

The present invention further relates to a process for obtaining these lower density absorbent foams by polymerizing a specific type of water-in-oil emulsion or HIPE having a relatively small amount of an oil phase and a relatively greater amount of a water phase. This process comprises the steps of A) forming a water-in-oil emulsion from:
  1) an oil phase comprising:
    a) from about 85 to about 98% by weight of a monomer component capable of forming a copolymer having a Tg of about 35° C. or lower, the monomer component comprising:
      i) from about 45 to about 70% by weight of at least one substantially water-insoluble monofunctional monomer capable of forming an atactic amorphous polymer having a Tg of about 25° C. or lower;
      ii) from about 10 to about 30% by weight of at least one substantially water-insoluble monofunctional comonomer capable of imparting toughness about equivalent to that provided by styrene;
      iii) from about 5 to about 25% by weight of a first substantially water-insoluble, polyfunctional crosslinking agent selected from divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; and
      iv) from 0 to about 15% by weight of a second substantially water-insoluble, polyfunctional crosslinking agent selected from polyfunctional acrylates, methacrylates, acrylamides, methacrylamides, and mixtures thereof; and
    b) from about 2 to about 15% by weight of an emulsifier component which is soluble in the oil phase and which is capable of forming a stable water-in-oil emulsion, the emulsifier component comprising a primary emulsifier having at least about 40% by weight emulsifying components selected from diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and
  2) a water phase comprising an aqueous solution containing: (a) from about 0.2 to about 20% by weight of a water-soluble electrolyte; and (b) an effective amount of a polymerization initiator;
  3) a volume to weight ratio of water phase to oil phase in the range of from about 55:1 to about 100:1; and
B) polymerizing the monomer component in the oil phase of the water-in-oil emulsion to form a polymeric foam material.

The polymeric foam material can be subsequently dewatered to the extent that a collapsed, polymeric foam material is formed that will re-expand upon contact with aqueous fluids.

The process of the present invention allows the formation of these lower density foams from HIPE as the result of a combination of two factors. One is the use of more robust emulsifiers, in particular diglycerol monooleate, diglycerol monoisostearate, and sorbitan monooleate emulsifiers having higher levels of interfacially active components. These more robust emulsifiers can stabilize the HIPE at these very high water-to-oil ratios, even when the HIPE is poured and/or polymerized at relatively high temperatures. The other is a balanced formulation of the monomer component with more polyfunctional crosslinking agent and less of the monomer conferring polystyrene-like toughness to achieve the desired targets for strength under compressive load without sacrificing tear resistance or resilience to an unacceptable degree. The inclusion of a second crosslinking agent, and in particular the diacrylates and dimethacrylates of a diol having at least 2, more preferably at least 4, most preferably 6, carbon atoms, is particularly useful in making foams with the desired properties.

BRIEF DESCRIPTION OF THE DRAWINGS

FIG. 7 of the drawings represents a blown-apart view of the components of a diaper structure also of dual layer core configuration having an hourglass-shaped fluid acquisition layer overlying an absorbent foam fluid storage/distribution layer with a modified hourglass shape.

DETAILED DESCRIPTION OF THE INVENTION

I. Low Density Polymeric Foam

A. General Foam Characteristics

Polymeric foams according to the present invention useful in absorbent articles and structures are those which are relatively open-celled. This means the individual cells of the foam are in complete, unobstructed communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2. For purposes of the present invention, a foam material is "open-celled" if at least 80% of the cells in the foam structure that are at least 1 µm in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the TEST METHODS section of copending U.S. application Ser. No. 989,270 (Dyer et al), filed Dec. 11, 1992, which is incorporated by reference. Foams which are useful as absorbents in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm.

The polymeric foams of the present invention can be prepared in the form of collapsed (i.e. unexpanded), polymeric foams that, upon contact with aqueous fluids, expand and absorb such fluids. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state.

Figure 2:
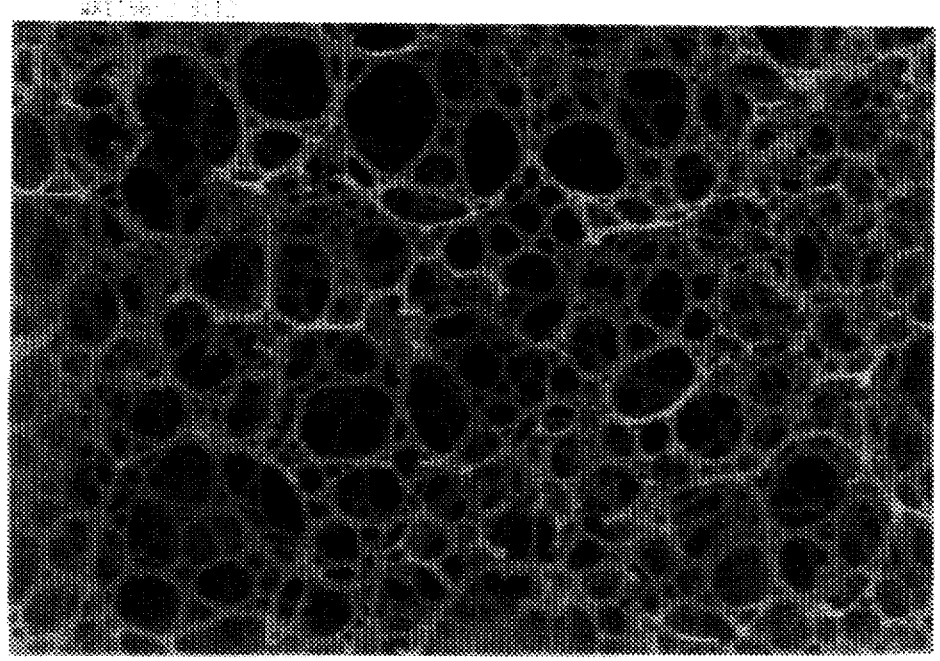
FIG. 2 of the drawings is a photomicrograph (1000 X magnification) of the foam of FIG. 1.
Figure 3:
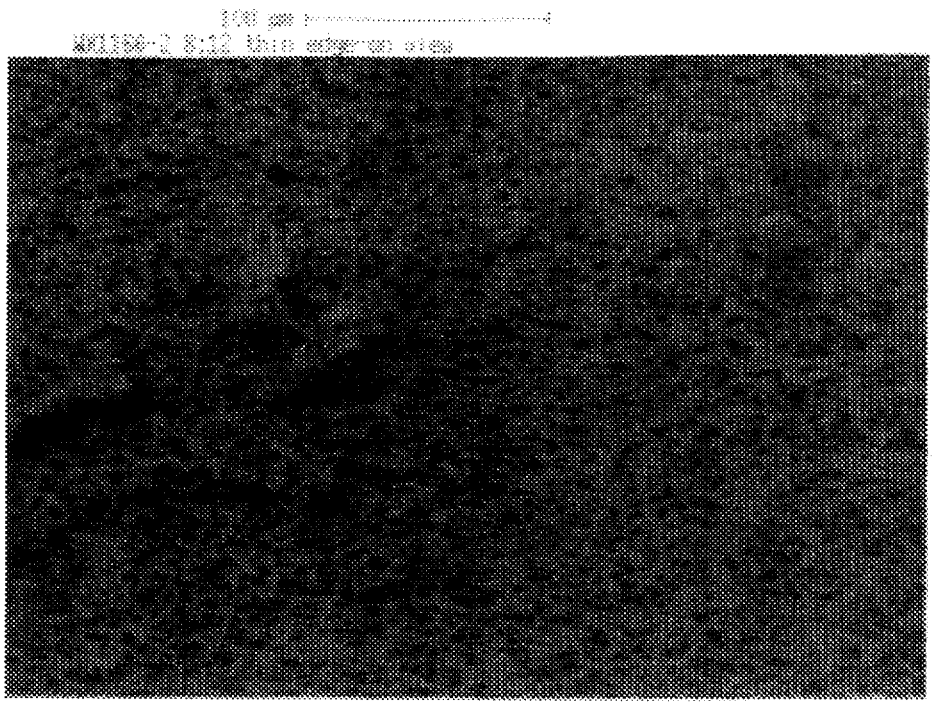
FIG. 3 of the drawings is a photomicrograph (250 X magnification) of an edge view of a cut section of another representative absorbent polymeric foam according to the present invention in its collapsed state from HIPE poured at 44° C. and having the same water-to-oil weight ratio, monomer component weight ratio and 6% DGMO emulsifier as the HIPE of FIG. 1.
Figure 4:
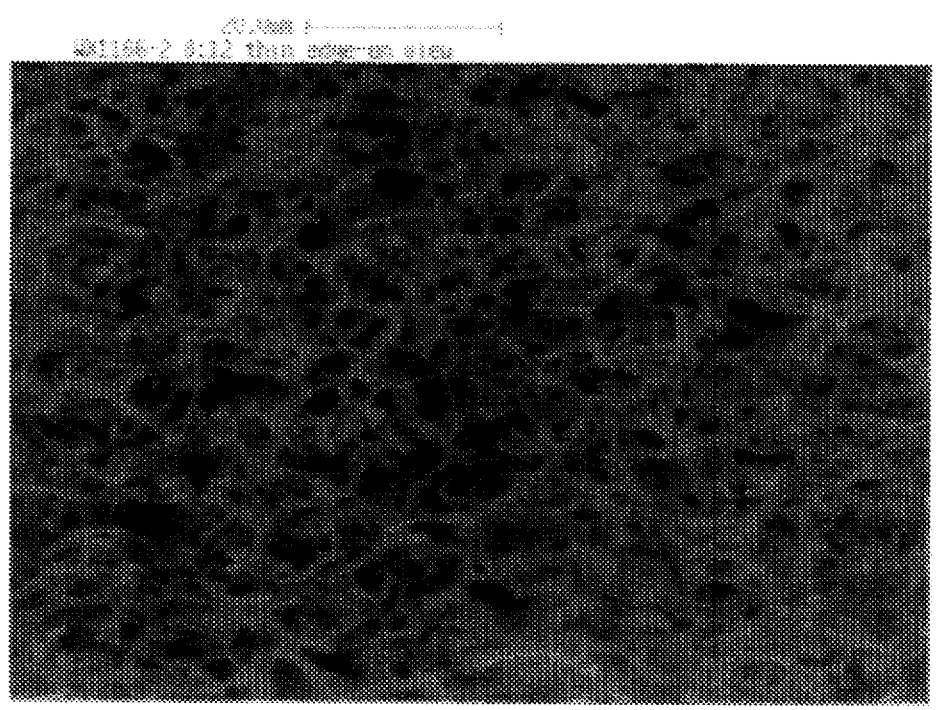
FIG. 4 of the drawings is a photomicrograph (1000 X magnification) of the foam of FIG. 3.

The cellular structure of a representative collapsed HIPE foam from which water has been expressed by compression is shown in the photomicrograph of FIGS. 3 and 4. As shown in these Figures, the cellular structure of the foam is distorted, especially when compared to the expanded HIPE foam structures shown in FIGS. 1 and 2. As can also be seen in FIGS. 3 and 4, the voids or pores (dark areas) in the collapsed foam structure have been flattened or elongated.

Following compression and/or thermal drying/vacuum dewatering, the collapsed polymeric foam can reexpand when wetted with aqueous fluids. Surprisingly, these polymeric foams remain in this collapsed, or unexpanded state, for significant periods of time, e.g., up to at least about 1 year. The ability of these polymeric foams to remain in this collapsed/unexpanded state is believed to be due to the capillary forces, and in particular the capillary pressures developed within the foam structure. As used herein, "capillary pressures" refers to the pressure differential across the liquid/air interface due to the curvature of meniscus within the narrow confines of the pores in the foam. [See Chatterjee, "Absorbency," *Textile Science and Technology*, Vol. 7, 1985, p. 36.]

After compression, and/or thermal drying/vacuum dewatering to a practicable extent, these polymeric foams have residual water that includes both the water of hydration associated with the hydroscopic, hydrated salt incorporated therein, as well as free water absorbed within the foam. This residual water (assisted by the hydrated salts) is believed to exert capillary pressures on the resulting collapsed foam structure. Collapsed polymeric foams of the present invention can have residual water contents of at least about 4%, typically from about 4 to about 40%, by weight of the foam when stored at ambient conditions of 72° F. (22° C.) and 50% relative humidity. Preferred collapsed polymeric foams have residual water contents of from about 5 to about 25% by weight of the foam.

A key parameter of these foams is their glass transition temperature (Tg). The Tg represents the midpoint of the transition between the glassy and rubbery states of the polymer. Foams that have a higher Tg than the temperature of use can be very strong but will also be very rigid and potentially prone to fracture. Such foams also typically take a long time to recover to the expanded state when wetted with aqueous fluids colder than the Tg of the polymer after having been stored in the collapsed state for prolonged periods. The desired combination of mechanical properties, specifically strength and resilience, typically necessitates a fairly selective range of monomer types and levels to achieve these desired properties.

For foams of the present invention, the Tg should be as low as possible, so long as the foam has acceptable strength at in-use temperatures. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean an incomplete transition at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression when wetted with aqueous fluids. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in the Test Methods section hereafter).

B. Capillary Pressures and Forces Within Foam Structure

In its collapsed state, the capillary pressures developed within the foam structure at least equal the forces exerted by the elastic recovery or modulus of the compressed polymer. In other words, the capillary pressure necessary to keep the collapsed foam relatively thin is determined by the countervailing force exerted by the compressed polymeric foam as it tries to "spring back." The elastic recovery tendency of polymeric foams can be estimated from stress-strain experiments where the expanded foam is compressed to about ⅙ (17%) of its original, expanded thickness and then held in this compressed state until a relaxed stress value is measured. Alternatively, and for the purposes of the present invention, the relaxed stress value is estimated from measurements on the polymeric foam in its collapsed state when in contact with aqueous fluids, e.g., water. This alternative relaxed stress value is hereafter referred to as the "expansion pressure" of the foam. The expansion pressure for collapsed polymeric foams of the present invention is about 30 kiloPascals (kPa) or less and typically from about 7 to about 20 kPa. A detailed description of a procedure for estimating the expansion pressure of foams is set forth in the TEST METHODS section of copending U.S. application Ser. No. 989,270 (Dyer et al), filed Dec. 11, 1992, which is incorporated by reference.

For the purposes of the present invention, it has been found that the specific surface area per foam volume is particularly useful for empirically defining foam structures that will remain in a collapsed state. See copending U.S. application Ser. No. 989,270 (Dyer et al), filed Dec. 11, 1992 (herein incorporated by reference), where specific area per foam volume is discussed in detail. "Specific surface area per foam volume" refers to the capillary suction specific surface area of the foam structure times its foam density in the expanded state. This specific surface area per foam volume value is characterized as "empirical" in that it is derived from (a) the capillary suction specific surface area that is measured during wetting of the dried foam structure, and (b) the density of the expanded foam structure after wetting to saturation, rather than by direct measurement of the dried, collapsed foam structure. Even so, it has been found that certain minimum specific surface area per foam volume values are correlatable to the ability of the foam structure to remain in a collapsed state. Polymeric foams according to the present invention having specific surface area per foam volume values of at least about 0.025 m$^2$/cc, preferably at least about 0.05 m$^2$/cc, most preferably at least about 0.07 m$^2$/cc, have been found empirically to remain in a collapsed state.

"Capillary suction specific surface area" is, in general, a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam and by the density of the polymer, and is thus a way of quantifying the total amount of solid surface provided by the foam network to the extent that such a surface participates in absorbency.

The capillary suction specific surface area is particularly relevant to whether adequate capillary pressures are developed within the foam structure to keep it in a collapsed state until wetted with aqueous fluids. The capillary pressure developed within the foam structure is proportional to the capillary suction specific surface area. Assuming other factors such as the foam density and adhesion tension are constant, this means that, as the capillary suction specific surface area is increased (or decreased), the capillary pressure within the foam structure also increases (or decreases) proportionately.

For purposes of the present invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section of copending U.S. patent application Ser. No 989,270(Dyer et al.), filed Dec. 11, 1992, which is incorporated by reference. Any reasonable alternative method for determining capillary suction specific surface area can also be utilized.

The collapsed polymeric foams of the present invention useful as absorbents are those that have a capillary suction specific surface area of at least about 3 $m^2/g$. Typically, the capillary suction specific surface area is in the range from about 3 to about 15 $m^2/g$, preferably from about 4 to about 13 $m^2/g$, most preferably from about 5 to about 11 $m^2/g$. Foams having such capillary suction specific surface area values (with expanded state densities of from about 0.010 to about 0.018 g/cc) will generally possess an especially desirable balance of absorbent capacity, fluid-retaining and fluid-wicking or distribution characteristics for aqueous fluids such as urine. In addition, foams having such capillary suction specific surface areas can develop a sufficient capillary pressure to keep the foam in a collapsed, unexpanded state until wetted with such aqueous fluids.

C. Free Absorbent Capacity

Another important property of the absorbent foams of the present invention is their free absorbent capacity. "Free absorbent capacity" is the total amount of test fluid (synthetic urine) which a given foam sample will absorb into its cellular structure per unit mass of solid material in the sample. To be especially useful in absorbent articles for absorbing aqueous fluids, the absorbent foams of the present invention should have a free absorbent capacity of from about 55 to about 100 mL, preferably from about 55 to about 75 mL of synthetic urine per gram of dry foam material. The procedure for determining the free absorbent capacity of the foam is described hereafter in the TEST METHODS section.

D. Expansion Factor

Upon exposure to aqueous fluids, the collapsed foams of the present invention expand and absorb the fluids. The foams of the present invention contain, in their expanded state, more fluid than most other foams. When these foams are compressively dewatered to a thickness of about ⅙ (17%) or less of their fully expanded thickness, they remain in even thinner states than is possible with prior HIPE foams, with a concomitant increase in storage efficiency and flexibility. This is attributable to the lower density of the expanded foams. The "expansion factor" for these foams is at least about 6X, i.e. the thickness of the foam in its expanded state is at least about 6 times the thickness of the foam in its collapsed state. The collapsed foams of the present invention typically have an expansion factor in the range of from about 6X to about 10X. By comparison, prior higher density foams typically have an expansion factor of only 4X to 5X.

For the purposes of the present invention, the relationship between expanded and collapsed thickness for compressively dewatered foams can be empirically predicted from the following equation:

$$\text{thickness}_{expanded} = \text{thickness}_{collapsed} \times 0.133 \times W{:}O\ \text{ratio}$$

where $\text{thickness}_{expanded}$ is the thickness of the foam in its expanded state;

$\text{thickness}_{collapsed}$ is the thickness of the foam in its collapsed state; and W:O ratio is the water-to-oil ratio of the HIPE from which the foam is made.

Thus, a typical foam made from an emulsion with water-to-oil ratio of 60:1 would have a predicted expansion factor of 8.0, i.e., an expanded thickness 8 times the collapsed thickness of the foam. The procedure for measuring the expansion factor is described hereafter in the TEST METHODS section.

E. Resistance to Compression Deflection

An important mechanical feature of the absorbent polymeric foams of the present invention is their strength in their expanded state, as determined by its resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as absorbents in absorbent articles such as diapers, the foams of s the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams of the present invention can be quantified by determining the amount of strain produced in a sample of saturated foam held under a certain confining pressure for a specified temperature and period of time. The method for carrying out this particular type of test is described hereafter in the TEST METHODS section. Foams useful as absorbents are those which exhibit a RTCD such that a confining pressure of 5.1 kPa produces a strain of typically about 40% or less compression of the foam structure when it has been saturated to its free absorbent capacity with synthetic urine having a surface tension of 65±5 dynes/cm. Preferably the strain produced under such conditions will be in the range from about 2 to about 25%, more preferably from about 4 to about 15%, most preferably from about 6 to about 10%.

F. Other Properties of Polymeric Foam

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

Figure 1:
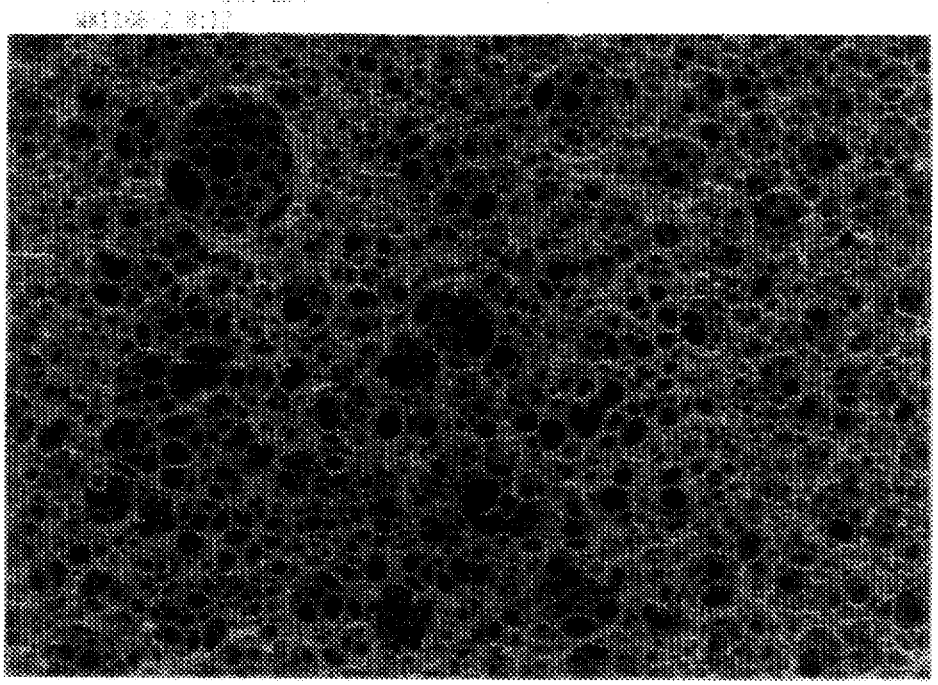
FIG. 1 of the drawings is a photomicrograph (250 X magnification) of an edge view of a cut section of a representative absorbent polymeric foam according to the present invention in its expanded state made from HIPE having a 56:1 water-to-oil weight ratio and poured at 44° C., and where the monomer component consisted of a 7:22:63:8 weight ratio of styrene:technical grade divinyl benzene (about 55% DVB and about 45% ethyl styrene):2-ethylhexyl acrylate:1,4-butanediol dimethacrylate, and where 6% (by weight of the oil phase) of diglycerol monooleate (DGMO) emulsifier was used.

A number of techniques are available for determining the average cell size of foams. The most useful technique, however, for determining cell size in foams involves a simple measurement based on the scanning electron photomicrograph of a foam sample. FIG. 1, for example, shows a typical HIPE foam structure according to the present invention in its expanded state. Superimposed on the photomicrograph is a scale representing a dimension of 20 µm. Such a scale can be used to determine average cell size via an image analysis procedure.

The cell size measurements given herein are based on the number average cell size of the foam in its expanded state, e.g., as shown in FIG. 1. The foams useful as absorbents for aqueous fluids in accordance with the present invention will preferably have a number average cell size of about 50 µm or less, and typically from about 5 to about 35 µm.

"Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the TEST METHODS section of copending U.S. application Ser. No. 989,270 (Dyer et al), filed Dec. 11, 1992 (herein incorporated by reference) is one method that can be employed for density determination. In its collapsed state, polymeric foams of the present invention useful as absorbents have dry basis density values in the range of from about 0.1 to about 0.2 g/cc, preferably from about 0.11 to about 0.15 g/cc, and most preferably from about 0.12 to about 0.14 g/cc. In its expanded state, polymeric foams of the present invention useful as absorbents have dry basis density values in the range of from about 0.010 to about 0.018 g/cc, preferably from about 0.013 to about 0.018 g/cc.

Suitable absorbent foams will in general exhibit especially desirable and useful aqueous fluid handling and absorbency characteristics. The fluid handling and absorbency characteristics that are most relevant for absorbent foams are: A) the rate of vertical wicking of fluid through the foam structure; B) the absorbent capacity of the foam at specific reference wicking heights; and C) the ability of the absorbent foam structures to drain (partition) fluid from competing absorbent structures with which the foam can be in contact.

Vertical wicking, i.e., fluid wicking in a direction opposite from gravitational force, is an especially desirable performance attribute for absorbent foams herein. These foams will frequently be utilized in absorbent articles in a manner such that fluid to be absorbed must be moved within the article from a relatively lower position to a relatively higher position within the absorbent core of the article. Accordingly, the ability of these foams to wick fluid against gravitational forces is particularly relevant to their functioning as absorbent components in absorbent articles.

Vertical wicking is determined by measuring the time taken for a colored test liquid (e.g., synthetic urine) in a reservoir to wick a vertical distance of 5 cm through a test strip of foam of specified size. The vertical wicking procedure is described in greater detail in the TEST METHODS section of copending U.S. application Ser. No. 989,270 (Dyer et al), filed Dec. 11, 1992, (herein incorporated by reference), but is performed at 31° C., instead of 37° C. To be especially useful in absorbent articles for absorbing urine, the foam absorbents of the present invention will preferably wick synthetic urine (65±5 dynes/cm) to a height of 5 cm in no more than about 30 minutes. More preferably, the preferred foam absorbents of the present invention wick synthetic urine to a height of 5 cm in no more than about 5 minutes.

The vertical wicking absorbent capacity test measures the amount of test fluid per gram of absorbent foam that is held within each one inch (2.54 cm) vertical section of the same standard size foam sample used in the vertical wicking test. Such a determination is generally made after the sample has been allowed to vertically wick test fluid to equilibrium (e.g., after about 18 hours). Like the vertical wicking test, the vertical wicking absorbent capacity test is described in greater detail in the TEST METHODS section of copending U.S. application Ser. No. 989,270 (Dyer et al), filed Dec. 11, 1992, which is incorporated by reference.

Another important property of useful absorbent foams according to the present invention is their capillary absorption pressure. Capillary absorption pressure refers to the ability of the foam to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h. To be especially useful in absorbent articles for absorbing aqueous fluids, the preferred absorbent foams of the present invention will generally have a capillary absorption pressure of at least about 24.1 cm (9.5 inches). (Foams of the present invention typically have absorption pressures of from about 30 to about 40 cm.)

II. Preparation of Polymeric Foams from HIPE Having Relatively High Water-to-Oil Ratios A. In General Polymeric foams according to the present invention can be prepared by polymerization of certain water-in-oil emulsions having a relatively high ratio of water phase to oil phase commonly known in the art as "HIPEs." Polymeric foam materials which result from the polymerization of such emulsions are referred to hereafter as "HIPE foams."

The relative amounts of the water and oil phases used to form the HIPEs are, among many other parameters, important in determining the structural, mechanical and performance properties of the resulting polymeric foams. In particular, the ratio of water to oil in the emulsion can influence the density, cell size, and capillary suction specific surface area of the foam and dimensions of the struts that form the foam. The emulsions used to prepare the HIPE foams of the present invention will generally have a volume to weight ratio of water phase to oil phase in the range of from about 55:1 to about 100:1, more preferably from about 55:1 to about 75:1, most preferably from about 55:1 to about 65:1.

1. Oil Phase Components

The continuous oil phase of the HIPE comprises monomers that are polymerized to form the solid foam structure. This monomer component is formulated to be capable of forming a copolymer having a Tg of about 35° C. or lower, and typically from about 150 to about 30° C. (The method for determining Tg by Dynamic Mechanical Analysis (DMA) is described hereafter in the TEST METHODS section.) This monomer component includes: (a) at least one monofunctional monomer whose atactic amorphous polymer has a Tg of about 25° C. or lower (see Brandup, J.; Immergut, E. H. "Polymer Handbook", 2nd Ed., Wiley-Interscience, New York, N.Y., 1975, III-139.); (b) at least one monofunctional comonomer to improve the toughness or tear resistance of the foam; (c) a first polyfunctional crosslinking agent; and (d) optionally a second polyfunctional crosslinking agent. Selection of particular types and amounts of monofunctional monomer(s) and comonomer(s) and polyfunctional cross-linking agent(s) can be important to the realization of absorbent HIPE foams having the desired combination of structure, mechanical, and fluid handling properties which render such materials suitable for use in the invention herein.

The monomer component comprises one or more monomers that tend to impart rubber-like properties to the resulting polymeric foam structure. Such monomers can produce high molecular weight (greater than 10,000) atactic amorphous polymers having Tgs of about 25° C. or lower. Monomers of this type include, for example, the ($C_4$–$C_{14}$) alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate, tetradecyl acrylate; aryl and alkaryl acrylates such as benzyl acrylate and nonylphenyl acrylate; the ($C_6$–$C_{16}$) alkyl methacrylates such as hexyl methacrylate, octyl methacrylate, nonyl methacrylate, decyl methacrylate, isodecyl methacrylate, dodecyl (lauryl) methacrylate, tetradecyl methacrylate, acrylamides such as N-octadecyl acrylamide, ($C_4$–$C_{12}$) alkyl styrenes such as p-n-octylstyrene, and combinations of such monomers. Of these monomers, isodecyl acrylate, dodecyl acrylate and 2-ethylhexyl acrylate are the most preferred. The monofunctional monomer(s) will generally comprise 45 to about 70%, more preferably from about 50 to about 65%, by weight of the monomer component.

The monomer component utilized in the oil phase of the HIPEs also comprises one or more monofunctional comonomers capable of imparting toughness about equivalent to that provided by styrene to the resulting polymeric foam structure. Tougher foams exhibit the ability to deform substantially without failure. These monofunctional comonomer types can include styrene-based comonomers (e.g., styrene and ethyl styrene) or other monomer types such as methyl methacrylate where the related homopolymer is well known as exemplifying toughness. The preferred monofunctional comonomer of this type is a styrene-based monomer with styrene and ethyl styrene being the most preferred monomers of this kind. The monofunctional "toughening" comonomer will normally comprise from about 10 to about 30%, preferably from about 15% to about 23%, most preferably from about 18% to about 22%, by weight of the monomer component.

In certain cases, the "toughening" comonomer can also impart the desired rubber-like properties to the resultant polymer. The $C_4$–$C_{12}$ alkyl styrenes, and in particular p-n-octylstyrene, are examples of such comonomers. For such comonomers, the amount that can be included in the monomer component will be that of the typical monomer and comonomer combined.

The monomer component also contains a first (and optionally second) polyfunctional crosslinking agent. As with the monofunctional monomers and comonomers, selection of the particular type and amount of crosslinking agents is very important to the eventual realization of preferred polymeric foams having the desired combination of structural, mechanical, and fluid-handling properties.

The first polyfunctional crosslinking agent can be selected from a wide variety of monomers containing two or more activated vinyl groups, such as divinylbenzenes, trivinyl benzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mires thereof. Divinylbenzene is typically available as a mixture with ethyl styrene in proportions of about 55:45. These proportions can be modified so as to enrich the oil phase with one or the other component. Generally, it is advantageous to enrich the mixture with the ethyl styrene component while simultaneously reducing the amount of styrene in the monomer blend. The preferred ratio of divinylbenzene to ethyl styrene is from about 30:70 to 55:45, most preferably from about 35:65 to about 45:55. The inclusion of higher levels of ethyl styrene imparts the required toughness without increasing the Tg of the resulting copolymer to the degree that styrene does. This first cross-linking agent can generally be included in the oil phase of the HIPE in an amount of from about 5 to about 25%, more preferably from about 12 to about 18%, most preferably from about 12% to about 16%, by weight of the monomer component (100% basis).

The optional second crosslinking agent can be selected from polyfunctional acrylates, methacrylates, acrylamides, methacrylamides, and mixtures thereof These include di-, tri-, and tetra-acrylates, as well as di-, tri-, and tetra-methacrylates, di-, tri-, and tetra-acrylamides, as well as di-, tri-, and tetra- methacrylamides; and mixtures of these crosslinking agents. Suitable acrylate and methacrylate crosslinking agents can be derived from diols, triols and tetraols that include 1,10-decanediol, 1,8-octanediol, 1,6-hexanediol, 1,4-butanediol, 1,3-butanediol, 1,4-but-2-enediol, ethylene glycol, diethylene glycol, trimethylolpropane, pentaerythritol, hydroquinone, catechol resorcinol triethylene glycol, polyethylene glycol, sorbitol and the like. (The acrylamide and methacrylamide crosslinking agents can be derived from the equivalent diamines, triamines and tetramines). The preferred diols have at least 2, more preferably at least 4, most preferably 6, carbon atoms. This second crosslinking agent can generally be included in the oil phase of the HIPE in an amount of from 0 to about 15%, preferably from about 7 to about 13%, by weight of the monomer component.

Without being bound by theory, it is believed this second crosslinking agent generates a more homogeneously crosslinked structure that develops strength more efficiently than using either the first or the second crosslinker alone at comparable levels. The second crosslinker also has the effect of broadening the glass-to-rubber transition region. This broader transition region can be tailored to meet specific strength and resilience requirements at in-use temperatures by controlling the relative amount of the two crosslinker types employed. Thus, a foam containing only the first type of crosslinker will exhibit a relatively narrow transition region that can be useful if higher resilience is desired and if the Tg is very close to the final in-use temperature. Increasing the amount of the second crosslinker serves to broaden the transition region, even if the actual transition temperature itself has not changed.

The major portion of the oil phase of the HIPEs will comprise the aforementioned monomers, comonomers and crosslinking agents. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase of the HIPE is an emulsifier component that comprises at least a primary emulsifier. Suitable primary emulsifiers have been found to be those which: (1) are soluble in the oil phase of the HIPE; (2) provide a minimum oil phase/water phase interfacial tension (IFT) of from about 0.06 to about 5 dyne/cm, preferably from about 0.1 to about 3 dyne/cm; (3) provide a critical aggregate concentration (CAC) of about 5 wt. % or less, preferably about 3 wt. % or less; (4) form HIPEs that are sufficiently stable against coalescence at the relevant drop sizes and the relevant process conditions (e.g., HIPE formation and polymerization temperatures); and (5) desirably have a high concentration of "interfacially active" component(s) capable of lowering the interfacial tension between the oil and water phases of the HIPE. While not being bound by theory, it is believed that the concentration of interfacially active components needs to be sufficiently high to provide at least approximately monolayer coverage to internal oil phase droplets at the preferred drop sizes, water:oil ratios, and emulsifier levels. Typically, these primary emulsifiers: (6) have melt and/or solid-to-liquid crystalline phase-transition temperatures of about 30° C. or less; (7) are water dispersible; (8) are substantially water insoluble or at least do not appreciably partition into the water phase under the conditions of use. It is preferred that the primary emulsifier provide sufficient wettability when spread on a hydrophobic surface (e.g., the polymeric foam) such that the advancing contact angle for synthetic urine is less than (preferably substantially less than) 90°. (The method of measurement for IFT and CAC is described in the TEST METHODS section hereafter.) These primary emulsifiers also preferably hydrophilize the resulting polymeric foam. These primary emulsifiers typically comprise at least about 40%, preferably at least about 50%, more preferably at least about 70%, emulsifying components selected from diglycerol monoesters of branched $C_{16}-C_{24}$ fatty acids, linear unsaturated $C_{16}-C_{22}$ fatty acids, or linear saturated $C_{12}-C_{14}$ fatty acids, such as diglycerol monooleate (i.e., diglycerol monoesters of $C_{18:1}$ fatty acids), diglycerol monomyristate, diglycerol monoisostearate, and diglycerol monoesters of coconut fatty acids; sorbitan monoesters of branched $C_{16}-C_{24}$ fatty acids, linear unsaturated $C_{16}-C_{22}$ fatty acids, and linear saturated $C_{12}-C_{14}$ fatty acids, such as sorbitan monooleate, sorbitan monomyristate, and sorbitan monoesters derived from coconut fatty acids; diglycerol monoaliphatic ethers of branched $C_{16}-C_{24}$ alcohols, linear unsaturated $C_{16}-C_{22}$ alcohols, and linear saturated $C_{12}-C_{14}$ alcohols, and mixtures of these emulsifying components. The preferred primary emulsifiers are diglycerol monooleate (e.g., preferably greater than about 40%, more preferably greater than about 50%, most preferably greater than about 70% diglycerol monooleate), sorbitan monooleate (e.g., preferably greater than about 40%, more preferably greater than about 50%, most preferably greater than about 70% sorbitan monooleate), and diglycerol monoisostearate (e.g., preferably greater than about 40%, more preferably greater than about 50%, most preferably greater than about 70% diglycerol monoisostearate).

Diglycerol monoesters of linear saturated, linear unsaturated and branched fatty acids useful as emulsifiers in the present invention can be prepared by esterifying diglycerol with fatty acids, using procedures well known in the art. See, for example, the method for preparing polyglycerol esters disclosed in copending U.S. application Ser. No. 989,270 (Dyer et al), filed Dec. 11, 1992, which is incorporated by reference. Diglycerol can be obtained commercially or can be separated from polyglycerols that are high in diglycerol. Linear saturated, linear unsaturated and branched fatty acids can be obtained commercially. The mixed ester product of the esterification reaction can be fractionally distilled under vacuum one or more times to yield distillation fractions that are high in diglycerol monoesters. For example, a A CMS-15A (C.V.C. Products Inc.; Rochester, N.Y.) continuous 14 inch centrifugal molecular still can be used for fractional distillation. Typically, the polyglycerol ester feedstock, while being heated, is first metered through a degasser unit and then to the heated evaporator cone of the still, where the vacuum distillation takes place. Distillate is collected on the bell jar surface, which can be heated to facilitate distillate removal. Distillate and residue are continuously removed by transfer pumps. The fatty acid composition of the resultant mixed ester product can be determined using high resolution gas chromatography. See copending U.S. application Ser. No. 989,270 (Dyer et al), filed Dec. 11, 1992, which is incorporated by reference. Polyglycerol and polyglycerol ester distribution of the resultant mixed ester product can be determined by capillary supercritical chromatography. See copending U.S. application Ser. No. 989,270 (Dyer et al), filed Dec. 11, 1992, which is incorporated by reference.

Linear saturated, linear unsaturated or, branched diglycerol monoaliphatic ethers can also be prepared and their composition determined using procedures well known in the art. See also copending U.S. application Ser. No. 08/514,346 (Stephen A. Goldman et al), filed Aug. 9, 1995, which is incorporated by reference.

Sorbitan esters of linear, branched, and unsaturated fatty acids can be obtained commercially or prepared using methods known in the art. See, for example, U.S. Pat. No. 4,103,047 (Zaki et al), issued Jul. 25, 1978 (herein incorporated by reference), especially column 4, line 32 to column 5, line 13. The mixed sorbitan ester product can be fractionally vacuum distilled to yield compositions that are high in sorbitan monoesters. Sorbitan ester compositions can be determined by methods well known in the art such as small molecule gel permeation chromatography. See copending U.S. application Ser. No. 08/514,346 (Stephen A. Goldman et al), filed Aug. 9, 1995, (herein incorporated by reference), which describes the use of this method for polyglycerol monoaliphatic ethers.

In addition to these primary emulsifiers, secondary emulsifiers can be optionally included in the emulsifier component. These secondary emulsifiers are at least cosoluble with the primary emulsifier in the oil phase and can be included to: (1) increase the stability of the HIPE against coalescence of the dispersed water droplets, especially at higher water-to-oil ratios and higher HIPE formation and polymerization temperatures, (2) modify the minimum IFT between oil and water phases to within the range of from about 0.06 to about 5 dyne/cm, (3) lower the CAC of the emulsifier component, or (4) increase the concentration of interfacially active components. Suitable secondary emulsifiers can be zwitterionic types, including the phosphatidyl cholines and phosphatidyl choline-containing compositions such as the lecithins and aliphatic betaines such as lauryl betaine; cationic types, including the long chain $C_{12}$–$C_{22}$ dialiphatic, short chain $C_1$–$C_4$ dialiphatic quaternary ammonium salts such as ditallow dimethyl ammonium chloride, bistridecyl dimethyl ammonium chloride, and ditallow dimethyl ammonium methylsulfate, the long chain $C_{12}$–$C_{22}$ dialkoyl(alkenoyl)-2-hydroxyethyl, short chain $C_1$–$C_4$ dialiphatic quaternary ammonium salts such as ditallowoyl-2-hydroxyethyl dimethyl ammonium chloride, the long chain $C_{12}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate, the short chain $C_1$–$C_4$ dialiphatic, long chain $C_{12}$–$C_{22}$ monoaliphatic benzyl quaternary ammonium salts such as dimethyl stearyl benzyl ammonium chloride and dimethyl tallow benzyl ammonium chloride, the long chain $C_{12}$–$C_{22}$ dialkoyl(alkenoyl)-2-aminoethyl, short chain $C_1$–$C_4$ monoaliphatic, short chain $C_1$–$C_4$ monohydroxyaliphatic quaternary ammonium salts such as ditallowoyl-2-aminoethyl methyl 2-hydroxypropyl ammonium methyl sulfate and dioleoyl-2-aminoethyl methyl 2-hydroxyethyl ammonium methyl sulfate; anionic types including the dialiphatic esters of sodium sulfosuccinic acid such as the dioctyl ester of sodium sulfosuccinic acid and the bistridecyl ester of sodium sulfosuccinic acid, the amine salts of dodecylbenzene sulfonic acid; and mixtures of these secondary emulsifiers. These secondary emulsifiers can be obtained commercially or prepared using methods known in the art. The preferred secondary emulsifiers are ditallow dimethyl ammonium methyl sulfate and ditallow dimethyl ammonium methyl chloride. When these optional secondary emulsifiers are included in the emulsifier component, it is typically at a weight ratio of primary to secondary emulsifier of from about 50:1 to about 1:4, preferably from about 30:1 to about 2:1.

The oil phase used to form the HIPEs comprises from about 85 to about 98% by weight monomer component and from about 2 to about 15% by weight emulsifier component. Preferably, the oil phase will comprise from about 90 to about 97% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al), issued Mar. 1, 1994, which is incorporated by reference.

A preferred optional component is an antioxidant such as a Hindered Amine Light Stabilizer (HALS) such as bis-(1, 2,2,5,5-pentamethylpiperidinyl) sebacate (Tinuvin-765®) or a Hindered Phenolic Stabilizer (HPS) such as Irganox-1076® and t-butylhydroxyquinone. Another preferred optional component is a plasticizer such as dioctyl azelate, dioctyl sebacate or dioctyl adipate. Other optional components include fillers, colorants, fluorescent agents, opacifying agents, chain transfer agents, and the like.

2. Water Phase Components

The discontinuous water internal phase of the HIPE is generally an aqueous solution containing one or more dissolved components. One essential dissolved component of the water phase is a water-soluble electrolyte. The dissolved electrolyte minimizes the tendency of monomers, comonomers, and crosslinkers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in the present invention. Generally the electrolyte will be utilized in the water phase of the HIPEs in a concentration in the range of from about 0.2 to about 20% by weight of the water phase. More preferably, the electrolyte will comprise from about 1 to about 10% by weight of the water phase.

The HIPEs will also typically contain an effective amount of a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

3. Hydrophilizing Surfactants and Hydratable Salts

The polymer forming the HIPE foam structure will preferably be substantially free of polar functional groups. This means the polymeric foam will be relatively hydrophobic in character. These hydrophobic foams can find utility where the absorption of hydrophobic fluids is desired. Uses of this sort include those where an oily component is mixed with water and it is desired to separate and isolate the oily component, such as in the case of oil spills.

When these foams are to be used as absorbents for aqueous fluids such as juice spills, milk, and urine, they generally require treatment to render the foam relatively more hydrophilic. This can be accomplished by treating the HIPE foam with a hydrophilizing surfactant in a manner described more fully hereafter.

These hydrophilizing surfactants can be any material that enhances the water wettability of the polymeric foam surface. They are well known in the art, and can include a variety of surfactants, preferably of the nonionic type. They will generally be in a liquid form, and can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. Such surfactants can include all of those previously described for use as the oil phase emulsifier for the HIPE, such as diglycerol monooleate, sorbitan monooleate and diglycerol monoisostearate. Such hydrophilizing surfactants can be incorporated into the foam during HIPE formation and polymerization, or can be incorporated by treatment of the polymeric foam with a solution or suspension of the surfactant in a suitable carrier or solvent. In preferred foams, the hydrophilizing surfactant is incorporated such that residual amounts of the surfactant that remain in the foam structure are in the range from about 0.5 to about 10%, preferably from about 0.5 to about 6%, by weight of the foam.

Another material that is typically incorporated into the HIPE foam structure is a hydratable, and preferably hygroscopic or deliquescent, water soluble inorganic salt. Such salts include, for example, toxicologically acceptable alkaline earth metal salts. Salts of this type and their use with oil-soluble surfactants as the foam hydrophilizing agent is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts. These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.1% by weight of the foam, and typically in the range of from about 0.1 to about 12%, preferably from about 7 to about 10%, by weight of the foam.

Treatment of these relatively hydrophobic foams with hydrophilizing surfactants (with or without hydratable salts) will typically be carried out to the extent necessary to impart suitable hydrophilicity to the foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the polymeric foam will be suitably hydrophilic, and will include residual water-phase liquid containing or depositing sufficient amounts of calcium chloride to render the foam hydrophilic, even after the polymeric foam has been dewatered or dried as described hereafter.

B. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing surfactant and/or hydratable salt to deposit any needed hydrophilizing surfactant/ hydratable salt, and 4) thereafter dewatering this polymeric foam structure.

1. Formation of HIPE

The HIPE is formed by combining the oil and water phase components in the previously specified ratios. The oil phase will typically contain the requisite monomers, comonomers, crosslinkers, and emulsifiers, as well as optional components such as plasticizers, antioxidants, flame retardants, and chain transfer agents. The water phase will typically contain electrolytes and polymerization initiators.

The HIPE can be formed from the combined oil and water phases by subjecting these combined phases to shear agitation. Shear agitation is generally applied to the extent and for a time period necessary to form a stable emulsion. Such a process can be conducted in either batchwise or continuous fashion and is generally carried out under conditions suitable for forming an emulsion where the water phase droplets are dispersed to such an extent that the resulting polymeric foam will have the requisite structural characteristics. Emulsification of the oil and water phase combination will frequently involve the use of a mixing or agitation device such as a pin impeller.

One preferred method of forming HIPE involves a continuous process that combines and emulsifies the requisite oil and water phases. In such a process, a liquid stream comprising the oil phase is formed. Concurrently, a separate liquid stream comprising the water phase is also formed. The two separate streams are then combined in a suitable mixing chamber or zone such that the requisite water to oil phase weight ratios previously specified are achieved.

In the mixing chamber or zone, the combined streams are generally subjected to shear agitation provided, for example, by a pin impeller of suitable configuration and dimensions. Shear will typically be applied to the combined oil/water phase stream at an appropriate rate. Once formed, the stable liquid HIPE can then be withdrawn from the mixing chamber or zone. This preferred method for forming HIPEs via a continuous process is described in greater detail in U.S. Pat. No. 5,149,720 (DesMarais et al), issued Sep. 22, 1992, which is incorporated by reference. See also copending U.S. application Ser. No. 08/370,694 (Thomas A. DesMarais), filed Jan. 10, 1995, (herein incorporated by reference), which describes an improved continuous process having a recirculation loop for the HIPE.

2. Polymerization/Curing of the HIPE

The HIPE formed will generally be collected or poured in a suitable reaction vessel, container or region to be polymerized or cured. In one embodiment, the reaction vessel comprises a tub constructed of polyethylene from which the eventually polymerized/cured solid foam material can be easily removed for further processing after polymerization/ curing has been carried out to the extent desired. The temperature at which the HIPE is poured into the vessel is preferably approximately the same as the polymerization/ curing temperature.

Suitable polymerization/curing conditions will vary depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at elevated temperatures above about 30° C., more preferably above about 35° C., for a time period ranging from about 2 to about 64 hours, more preferably from about 4 to about 48 hours. The HIPE can also be cured in stages such as described in U.S. Pat. No. 5,189,070 (Brownscombe et al), issued Feb. 23, 1993, which is herein incorporated by reference.

One particular advantage of the more robust emulsifier systems used in these HIPEs is that the polymerization/ curing conditions can be carried out at more elevated temperatures of about 50° C. or higher, more preferably about 60° C. or higher. Typically, the HIPE can be polymerized/cured at a temperature of from about 60° to about 99° C., more typically from about 65° to about 95° C.

A porous water-filled open-celled HIPE foam is typically obtained after polymerization/curing in a reaction vessel, such as a tub. This polymerized HIPE foam is typically cut or sliced into a sheet-like form. Sheets of polymerized HIPE foam are easier to process during subsequent treating/washing and dewatering steps, as well as to prepare the HIPE foam for use in absorbent articles. The polymerized HIPE foam is typically cut/sliced to provide a cut thickness in the range of from about 0.08 to about 2.5 cm. Subsequent dewatering by compressing the foam in the z-direction typically leads to collapsed HIPE foams having a thickness in the range of from about 10 to about 17% of its cut thickness.

3. Treating/Washing HIPE Foam

The polymerized HIE foam formed will generally be filled with residual water phase material used to prepare the HIPE. This residual water phase material (generally an aqueous solution of electrolyte, residual emulsifier, and polymerization initiator) should be at least partially removed prior to further processing and use of the foam. Removal of this original water phase material will usually be carried out by compressing the foam structure to squeeze out residual liquid and/or by washing the foam structure with water or other aqueous washing solutions. Frequently several compressing and washing steps, e.g., from 2 to 4 cycles, can be used.

After the original water phase material has been removed to the extent required, the HIPE foam, if needed, can be treated, e.g., by continued washing, with an aqueous solution of a suitable hydrophilizing surfactant and/or hydratable salt. Hydrophilizing surfactants and hydratable salts that can be employed have been previously described. As noted, treatment of the HIPE foam with the hydrophilizing surfactant/hydratable salt solution continues, if necessary, until the desired amount of hydrophilizing surfactant/hydratable salt has been incorporated and until the foam exhibits the desired adhesion tension value for any test liquid of choice.

4. Foam Dewatering

After the HIPE foam has been treated/washed, it will generally be dewatered. Dewatering can be achieved by compressing the foam to squeeze out residual water, by subjecting the foam, or the water therein to temperatures of from about 60° to about 200° C. or to microwave treatment, by vacuum dewatering or by a combination of compression and thermal drying/microwave/vacuum dewatering techniques. These HIPE foams are typically compressively dewatered to a thickness of about ⅙ (17%) or less of their fully expanded thickness. The dewatering step will generally be carried out until the HIPE foam is ready for use and is as dry as practicable. Frequently such compression dewatered foams will have a water (moisture) content of from about 50 to about 500%, more preferably from about 50 to about 200%, by weight on a dry weight basis. Subsequently, the compressed foams can be thermally dried to a moisture content of from about 5 to about 40%, more preferably from about 5 to about 15%, on a dry weight basis.

III. Uses of Polymeric Foams

A. In General

Polymeric foams according to the present invention are broadly useful as absorbent cores in disposable diapers, as well as other absorbent articles. These foams can also be employed as environmental waste oil sorbents; as absorbent components in bandages or dressings; to apply paint to various surfaces; in dust mop heads; in wet mop heads; in dispensers of fluids; in packaging; in shoes; in odor/moisture sorbents; in cushions; in gloves; and for many other uses.

B. Absorbent Articles

Polymeric foams of the present invention are particularly useful as at least a portion of the absorbent structures (e.g., absorbent cores) for various absorbent articles. By "absorbent article" herein is meant a consumer product that is capable of absorbing significant quantities of urine or other fluids (i.e., liquids), like aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The absorbent foam structures herein are particularly suitable for use in articles such as diapers, incontinence pads or garments, clothing shields, and the like.

In its simplest form, an absorbent article of the present invention need only include a backing sheet, typically relatively liquid-impervious, and one or more absorbent foam structures associated with this backing sheet. The absorbent foam structure and the backing sheet will be associated in such a manner that the absorbent s foam structure is situated between the backing sheet and the fluid discharge region of the wearer of the absorbent article. Liquid impervious backing sheets can comprise any material, for example polyethylene or polypropylene, having a thickness of about 1.5 mils (0.038 mm), which will help retain fluid within the absorbent article.

More conventionally, these absorbent articles will also include a liquid-pervious topsheet element that covers the side of the absorbent article that touches the skin of the wearer. In this configuration, the article includes an absorbent core comprising one or more absorbent foam structures of the present invention positioned between the backing sheet and the topsheet. Liquid-pervious topsheets can comprise any material such as polyester, polyolefin, rayon and the like that is substantially porous and permits body fluid to readily pass there through and into the underlying absorbent core. The topsheet material will preferably have no propensity for holding aqueous fluids in the area of contact between the topsheet and the wearer's skin.

The absorbent core of the absorbent article embodiments of the present invention can consist solely of one or more of these foam structures. For example, the absorbent core can comprise a single unitary piece of foam shaped as desired or needed to best fit the type of absorbent article in which it is to be used. Alternatively, the absorbent core can comprise a plurality of foam pieces or particles that can be adhesively bonded together or which can simply be constrained into an unbonded aggregate held together by an overwrapping of envelope tissue or by means of the topsheet and backing sheet of the absorbent article.

The absorbent core of the absorbent articles herein can also comprise other, e.g., conventional, elements or materials in addition to one or more absorbent foam structures of the present invention. For example, absorbent articles herein can utilize an absorbent core that comprises a combination, e.g., an air-laid mixture, of particles or pieces of the absorbent foam structures herein and conventional absorbent materials such as a) wood pulp or other cellulosic fibers, and/or, b) particles or fibers of polymeric gelling agents.

In one embodiment involving a combination of the absorbent foam herein and other absorbent materials, the absorbent articles can employ a multi-layer absorbent core configuration where a core layer containing one or more foam structures of the present invention can be used in combination with one or more additional separate core layers comprising other absorbent structures or materials. These other absorbent structures or materials, for example, can include air-laid or wet-laid webs of wood pulp or other cellulosic fibers. These other absorbent structures can also comprise other types of foams, e.g., absorbent foams or even sponges useful as fluid acquisition/distribution components such as those disclosed in copending U.S. application Ser. No. 08/370,695 (Keith J. Stone et al), filed Jan. 10, 1995, which is incorporated by reference. These other absorbent structures can also contain, for example up to 80% by weight, of particles or fibers of polymeric gelling agent of the type commonly used in absorbent articles that are to acquire and retain aqueous fluids. Polymeric gelling agents of this type and their use in absorbent articles are more fully described in U.S. Reissue Pat. No. 32,649 (Brandt et al), reissued Apr. 19, 1988, which is incorporated by reference.

An embodiment of these absorbent articles utilizes a multi-layer absorbent core having a fluid handling layer positioned in the fluid discharge region of the wearer of the article. This fluid-handling layer can be in the form of a high loft nonwoven, but is preferably in the form of a fluid acquisition/distribution layer comprising a layer of modified cellulosic fibers, e.g., stiffened curled cellulosic fibers, and optionally up to about 10% by weight of this fluid acquisition/distribution layer of polymeric gelling agent. The modified cellulosic fibers used in the fluid acquisition/ distribution layer of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,622 (Lash et al), issued Jun. 19, 1990, which is incorporated by reference.

These multi-layer absorbent cores also comprise a second, i.e., lower, fluid storage/redistribution layer comprising a foam structure of the present invention. For purposes of the present invention, an "upper" layer of a multi-layer absorbent core is a layer that is relatively closer to the body of the wearer, e.g., the layer closest to the article topsheet. The term "lower" layer conversely means a layer of a multi-layer absorbent core that is relatively further away from the body of the wearer, e.g., the layer closest to the article backsheet. This lower fluid storage/redistribution layer is typically positioned within the absorbent core so as to underlie the (upper) fluid-handling layer and be in fluid communication therewith. Absorbent articles that can utilize the absorbent foam structures of the present invention in a lower fluid storage/redistribution layer underlying an upper fluid acquisition/distribution layer containing stiffened curled cellulosic fibers are described in greater detail in the U.S. Pat. No. 5,147,345 (Young et al), issued Sep. 15, 1992 which is incorporated by reference. Multi-layer absorbent cores can also be made according to copending U.S. application Ser. No. 08/370,900 (Gary Dean Lavon et al), filed Jan. 10, 1995, (herein incorporated by reference), where the fluid storage/ redistribution layer comprises an absorbent foam according to the present invention.

Figure 5:
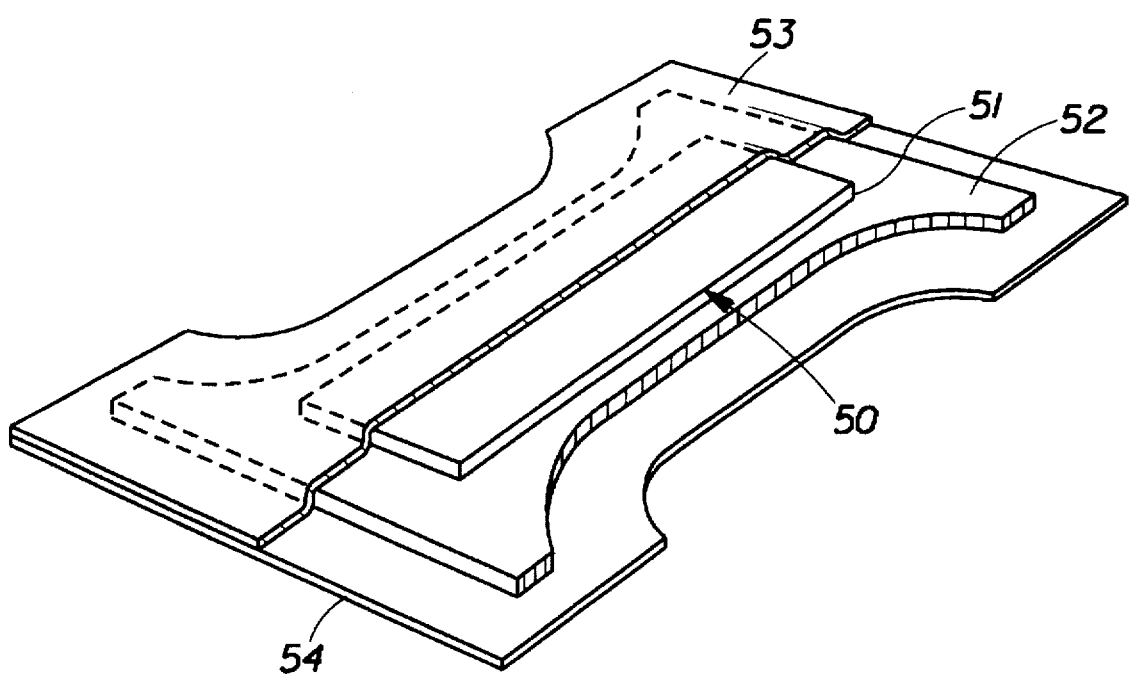
FIG. 5 of the drawings is a cutaway depiction of a disposable diaper that utilizes the absorbent polymeric foam of the present invention as an hourglass-shaped fluid storage/distribution component in an absorbent diaper core of dual-layer configuration.

Disposable diapers comprising the absorbent foam structures of the present invention can be made by using conventional diaper making techniques, but by replacing or supplementing the wood pulp fiber web ("airfelt") or modified cellulosic core absorbents typically used in conventional diapers with one or more foam structures of the present invention. Foam structures of the present invention can thus be used in diapers in single layer, or in various multiple layer core configurations as previously described. A representative disposable diaper embodiment of the present invention is illustrated by FIG. 5 of the drawings. Such a diaper includes an absorbent core 50, comprising an upper fluid acquisition layer 51, and an underlying fluid storage/redistribution layer 52 comprising an absorbent foam structure of the present invention. A topsheet 53 is superposed and co-extensive with one face of the core, and a liquid impervious backsheet 54 is superposed and coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another type of absorbent article which can utilize the absorbent foam structures of the present invention comprises form-fitting products such as training pants. Such form-fitting articles will generally include a nonwoven, flexible substrate fashioned into a chassis in the form of briefs or shorts. An absorbent foam structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article can comprise cloth or paper or other kinds of nonwoven substrate or formed films and can be elasticized or otherwise stretchable. Leg bands or waist bands of such training pants articles can be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pants products of this kind are described in U.S. Pat. No. 4,619,649 (Roberts), issued Oct. 28, 1986, which is incorporated by reference.

Figure 6:
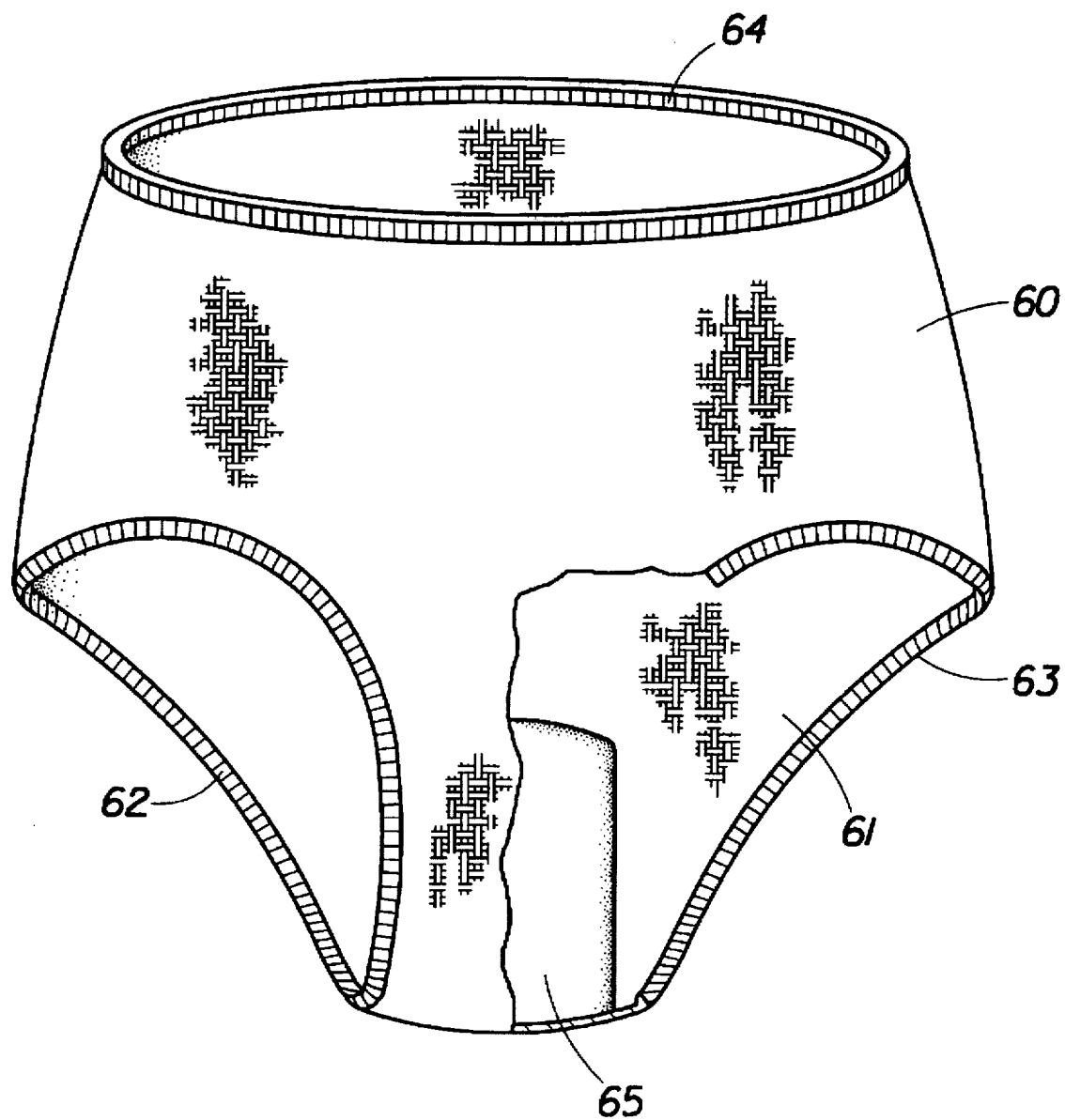
FIG. 6 of the drawings represents a cut-away view of a form-fitting article such as a disposable training pants product that employs an absorbent polymeric foam according to the present invention as an absorbent core.

A typical form-fitting article in the form of a disposable training pants product is shown in FIG. 6 of the drawings. Such a product comprises an outer layer 60 affixed to a lining layer 61 by adhesion along the peripheral zones thereof. For example, the inner lining 61 can be affixed to the outer layer 60, along the periphery of one leg band area 62, along the periphery of the other leg band area 63, and along the periphery of waistband area 64. Affixed to the crotch area of the article is a generally rectangular absorbent core 65 comprising an absorbent foam structure of the present invention.

IV. Test Methods

A. Dynamic Mechanical Analysis (DMA)

DMA is used to determine the Tgs of polymers including polymeric foams. Samples of the foams are sliced into blocks 3–5 mm in thickness and washed 3–4 times in distilled water, expressing the fluid through roller nips between each washing. The resulting foam blocks are allowed to dry in air. The dried foam slices are cored to yield a cylinders 25 mm in diameter. These cylinders are analyzed using a Rheometrics RSA-II dynamic mechanical analyzer set in compression mode using parallel plates 25 mm in diameter. Instrument parameters used were as follows:

Temperature step from ca. 85° C. to −40° C. in steps of 2.5° C.

Soak intervals between temperature changes of 125–160 seconds

Dynamic strain set at 0.1% to 1.0% (usually 0.7%)

Frequency set at 1.0 radians/second

Autotension set in static force tracking dynamic force mode with initial static force set at 5 g.

The glass transition temperature is taken as the maximum point of the loss tangent versus temperature curve.

B. Resistance to Compression Deflection (RTCD)

Resistance to compression deflection can be quantified by measuring the amount of strain (% reduction in thickness) produced in a foam sample which has been saturated and expanded with synthetic urine, after a confining pressure of 0.74 psi (5.1 kPa) has been applied to the sample. Resistance to Compression Deflection measurements are typically made on the same sample concurrently with the measurement of Free Absorbent Capacity and Expansion Factor as described below.

Jayco synthetic urine used in this method is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$, and 0.23 g $MgCl_2$ to 1.0 liters with distilled water. The salt mixture can be purchased from Endovations, Reading, Pa. (cat No. JA-0013 1-000-01).

The foam samples, Jayco synthetic urine and equipment used to make measurements are all equilibrated to a temperature of 31° C. All measurements are also performed at this temperature.

A foam sample sheet in its collapsed state is expanded and saturated to its free absorbent capacity by soaking in a bath of Jayco synthetic urine. After 3 minutes, a cylinder having a 1 in$^2$ (6.5 cm$^2$) circular surface area is cut out of the saturated, expanded sheet with a sharp circular die. The cylindrical sample is soaked in synthetic urine at 31° C. for a further 6 minutes. The sample is then removed from the synthetic urine and is placed on a flat granite base under a gauge suitable for measuring the sample thickness. The gauge is set to exert a pressure of 0.08 psi on the sample. Any gauge fitted with a foot having a circular surface area of at least 1 in$^2$ (6.5 cm$^2$) and capable of measuring thickness to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan).

After 2 to 3 min., the expanded thickness (X1) is recorded. A force is then applied to the foot so that the saturated foam sample is subjected to a pressure of 0.74 psi (5.1 kPa) for 15 minutes. At the end of this time, the gauge is used to measure the final sample thickness (X2). From the initial and final thickness measurements, the percent strain induced can be calculated for the sample as follows:

$[(X1-X2)/X1] \times 100 = \%$ reduction in thickness.

C. Free Absorbent Capacity

Free absorbent capacity can be quantified by measuring the amount synthetic urine absorbed in a foam sample which has been saturated and expanded with synthetic urine. Free Absorbent Capacity measurements are typically made on the same sample concurrently with the measurement of Resistance to Compression Deflection and Expansion Factor.

The foam samples and Jayco synthetic urine are equilibrated to a temperature of 31 ° C. Measurements are performed at ambient temperature.

A foam sample sheet in its collapsed state is expanded and saturated to its free absorbent capacity by soaking in a bath of Jayco synthetic urine. After 3 minutes, a cylinder having a 1 in$^2$ (6.5 cm$^2$) circular surface area is cut out of the saturated, expanded sheet with a sharp circular die. The cylindrical sample is soaked in synthetic urine at 31° C. for a further 3 minutes. The sample is then removed from the synthetic urine and is placed on a digital balance. Any balance fitted with a weighing pan having an area larger than that of the sample and with a resolution of 1 milligram or less can be employed. Examples of such balances are the Mettler PM 480 and Mettler PC 440 (Mettler Instrument Corp; Hightstown N.J.).

After determining the weight of the wet foam sample (Ww), it is placed between 2 fine plastic mesh screens on top of 4 disposable paper towels. The sample is squeezed 3 times by firmly rolling a plastic roller over the top screen. The sample is then removed, soaked in distilled water for approximately 2 minutes, and squeezed between mesh screens as before. It is then placed between 8 layers of disposable paper towels (4 on each side) and pressed with 20,000 lbs. of force in a Carver Laboratory Press. The sample is then removed from the paper towels, dried in a Fisher convection oven at 82° C. for 20 minutes, and its dry weight recorded (Wd).

The free absorbent capacity (FAC) is the wet weight (Ww), less the dry weight (Wd) divided by the dry weight (Wd), i.e., FAC=[(Ww−Wd)/Wd]

D. Expansion Factor

Expansion factor can be quantified by measuring the thickness of a foam sample in the collapsed state and in the expanded state. The ratio of the expanded thickness to the initial collapsed thickness is the expansion factor. The two measurements are conveniently run on the same sample concurrently with the measurement of RTCD and Free Absorbent Capacity as described above.

The foam samples, Jayco synthetic urine and equipment used are all equilibrated to a temperature of 31° C. All measurements are also performed at this temperature.

The foam sample in its collapsed state is placed on a flat granite base under a gauge suitable for measuring the sample thickness. The gauge is set up to exert a pressure of 0.08 psi on the sample. Any gauge fitted with a foot having a circular surface area of at least 1 in$^2$ (6.5 cm$^2$) and capable of measuring thickness to 0.0010 in (0.025 mm) can be employed. Examples of such gauges are an Ames model 482 (Ames Co.; Waltham, Mass.) or an Ono-Sokki model EG-225 (Ono-Sokki Co., Ltd.; Japan). The initial thickness is recorded (X0).

The foam sample is then expanded and saturated to its free absorbent capacity by soaking in a bath of Jayco synthetic urine. After 3 minutes, a cylinder having a 1 in$^2$ (6.5 cm$^2$) circular surface area is cut out of the saturated, expanded sheet with a sharp circular die. The cylindrical sample is soaked in synthetic urine at 31° C. for a further 6 minutes. The sample is then removed from the synthetic urine and placed on a flat granite base under a gauge suitable for measuring the sample thickness as above. After 2 to 3 min., the expanded thickness (X1) is recorded.

The expansion factor (EF) is calculated as EF=X1/X0.

E. Interfacial tension (IFT) method (Spinning Drop)

Interfacial Tension (IFT) is measured at 50° C. by the spinning drop method described in copending U.S. application Ser. No. 989,270 (Dyer et al), filed Dec. 11, 1992 (herein incorporated by reference), except that: (1) the monomer mixture used in preparing the oil phase contains styrene, divinylbenzene (55% technical grade), 2-ethylhexylacrylate, and 1,4-butanediol dimethacrylate in a weight ratio of 14:14:60:12; (2) the concentration of emulsifier in the oil phase is varied by dilution from an upper concentration of generally about 5–10 weight % down to a concentration where the IFT increases to a value that is at least about 10 dyne/cm greater than the minimum IFT, or about 18 dyne/cm, whichever is less; (3) a smooth line drawn through a plot of IFT versus log emulsifier concentration is used to determine the minimum IFT; (4) the Critical Aggregation Concentration (CAC) is determined by extrapolating the low-concentration, generally linear portion of the IFT versus log concentration plot (i.e., the portion of the curve typically used to calculate surface area per molecule at the interface, see for example Surfactants and Interfacial Phenomena, Second Edition, Milton J. Rosen, 1989, Pages 64–69) to higher concentration; the emulsifier concentration on this extrapolated line corresponding to the minimum IFT is taken as the CAC. Generally, an upper emulsifier concentration of about 5–10 weight % is used. Desirably, the upper emulsifier concentration used is at least about twice (more desirably at least about three times) the CAC of the emulsifier. For emulsifiers having a solubility in the oil phase at ambient-temperature of less than 5 wt. %, the upper concentration limit can be reduced as long as this concentration is still at least about twice the CAC of the emulsifier at 50° C.

F. Capillary Absorption Pressures

A capillary absorption isotherm curve is generated using the Vertical Wicking Absorbent Capacity test described in the TEST METHODS section of copending U.S. application Ser. No. 989,270 (Dyer et al), filed Dec. 11, 1992, which is incorporated by reference, except at 31° C. rather than 37° C. The curve is a plot of the absorbent capacity of each segment as a function of wicked height, using the distance from the top of the water reservoir to the midpoint of each segment for the height h. The capillary absorption pressure is taken as the height of the foam that has an absorbent capacity one-half of the foam's free absorbent capacity.

V. Specific Examples

These examples illustrate the specific preparation of collapsed HIPE foams according the present invention.

EXAMPLE 1

Preparation of Foam from a HIPE

A) HIPE Preparation

Anhydrous calcium chloride (36.32 kg) and potassium persulfate (189 g) are dissolved in 378 liters of water. This provides the water phase stream to be used in a continuous process for forming the HIPE.

To a monomer combination comprising styrene (420 g), divinylbenzene 55% technical grade (1320 g), 2-ethylhexylacrylate (3780 g), and 1,4-butanediol dimethacrylate (480 g) is added a high purity diglycerol monooleate (360 g), and Tinuvin 765 (30 g) [bis(1,2,2,5,5-pentamethylpiperidinyl)sebacate]. This diglycerol monooleate emulsifier is prepared following the general procedure for preparing polyglycerol esters described in copending U.S. application Ser. No. 989,270 (Dyer et al), filed Dec. 11, 1992. A polyglycerol composition comprising approximately 97% or greater diglycerol and 3% or less triglycerol (Solvay Performance Chemicals; Greenwich, Conn.) is esterified with fatty acids having a fatty acid composition comprising approximately 71% C18:1, 4% C18:2, 9% C16:1, 5% C16:0, and 11% other fatty acids (Emersol-233LL, Emery/Henkel) in a polyglycerol:fatty acid weight ratio of approximately 60:40, using sodium hydroxide as a catalyst at about 225° C. under conditions of mechanical agitation, nitrogen sparging, and gradually increasing vacuum, with subsequent phosphoric acid neutralization, cooling to about 85 C., and settling to reduce the level of unreacted polyglycerols. The polyglycerol ester reaction product is first fractionally distilled through two CMS-15A centrifugal molecular stills connected in series to reduce the levels of unreacted polyglycerols and fatty acids and then redistilled through the stills to yield distillation fractions high in diglycerol monoesters. Typical conditions for the final distillation pass are a feed rate of about 15 lb/hr, a degasser vacuum of about 21–26 microns, a bell jar vacuum of about 6–12 microns, a feed temperature of about 170° C., and a residue temperature of about 180° C. Distillation fractions high in diglycerol monoesters are combined, yielding a reaction product (as determined by supercritical fluid chromatography) comprising approximately 50% diglycerol monooleate, 27% other diglycerol monoesters, 20% polyglycerols, and 3% other polyglycerol esters. The resultant diglycerol monooleate emulsifier imparts a minimum oil phase/water phase interfacial tension value of approximately 1.0 dyne/cm and has a critical aggregation concentration of approximately 0.9 wt %. After mixing, the reaction product is allowed to settle overnight. The supernatant is withdrawn and used in the oil phase as the emulsifier in forming the HIPE. (About 20 g of a sticky residue is discarded.)

Separate streams of the oil phase (25° C.) and water phase (42°–44° C.) are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft holds 4 rows of pins. 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 3 parts water to 1 part oil. The dynamic mixing apparatus is vented to allow air to escape while filling the apparatus completely. The flow rates during filling are 1.89 g/sec oil phase and 5.68 cc/sec water phase.

Once the apparatus set-up is filled, agitation is begun in the dynamic mixer, with the impeller turning at 1800 RPM. The flow rate of the water phase is then steadily increased to a rate of 45.4 cc/sec and the oil phase flow rate is reduced to 0.82 g/sec over a time period of about 2 min. The back pressure created by the dynamic and static mixers at this point is 13.4 PSI (92 kPa). The impeller speed is then steadily decreased to a speed of 1200 RPM over a period of 120 sec. The back pressure drops to 5.4 PSI (37 kPa). At this point, the impeller speed is instantly increased to 1800 RPM. The system back pressure increases to 6.5 PSI (44 kPa) and remains constant thereafter. The resultant HIPE has a water-to-oil ratio of about 55:1.

B) Polymerization/Curing of HIPE

The HIPE from the static mixer is collected in a round polypropylene tub, 17 in. (43 cm) in diameter and 7.5 in. (10 cm) high, with a concentric insert made of Celcon plastic. The insert is 5 in. (12.7 cm) in diameter at its base and 4.75 in (12 cm) in diameter at its top and is 6.75 in. (17.14 cm) high. The HIPE-containing tubs are kept in a room maintained at 65° C. for 18 hours to cure and provide a polymeric HIPE foam.

C) Foam Washing and Dewatering

The cured HIPE foam is removed from the tubs. The foam at this point has residual water phase (containing dissolved emulsifiers, electrolyte, initiator residues, and initiator) about 50–60 times (50–60X the weight of polymerized monomers. The foam is sliced with a sharp reciprocating saw blade into sheets which are 0.145 inches (0.368 cm) in thickness. These sheets are then subjected to compression in a series of 2 porous nip rolls equipped with vacuum which gradually reduces the residual water phase content of the foam to about 6 times (6X) the weight of the polymerized monomers. At this point, the sheets are then resaturated with a 1.5% $CaCl_2$ solution at 60° C., are squeezed in a series of 3 porous nip rolls equipped with vacuum to a water phase content of about 4X. The $CaCl_2$ content of the foam is between 8 and 10%.

The HIPE foam remains compressed after the final nip at a thickness of about 0.019 in. (0.048 cm). The foam is then dried in air for about 16 hours. Such drying reduces the moisture content to about 9–17% by weight of polymerized material. At this point, the foam sheets are very drapeable. In the collapsed state, the density of the foam is about 0.14 g/cc. When expanded in Jayco synthetic urine, its free absorbent capacity is about 54 mL/g and has a glass transition temperature of 19° C.

EXAMPLE 2

Preparation of Foam from a HIPE

A) HIPE Preparation

Anhydrous calcium chloride (36.32 kg) and potassium persulfate (189 g) are dissolved in 378 L of water. This provides the water phase stream to be used in a continuous process for forming the HIPE.

To a monomer combination comprising distilled divinylbenzene (40% divinylbenzene and 60% ethyl styrene) (2100 g), 2-ethylhexylacrylate (3300 g), and hexanediol diacrylate (600 g) is added a very high purity diglycerol monooleate (360 g), and Tinuvin 765 (30 g). The diglycerol monooleate emulsifier (Grindsted Products; Brabrand, Denmark) comprises approximately 81% diglycerol monooleate, 1% other diglycerol monoesters, 3% polyglycerols, and 15% other polyglycerol esters, imparts a minimum oil phase/water phase interfacial tension value of approximately 2.5 dyne/cm and has a critical aggregation concentration of approximately 2.9 wt %. After mixing, this emulsifier mixture is allowed to settle overnight. No visible residue is formed and all of the mix is withdrawn and used in the oil phase as the emulsifier in forming the HIPE.

Separate streams of the oil phase (25° C.) and water phase (53°–55° C.) are fed to a dynamic mixing apparatus as in Example 1. A portion of the material exiting the dynamic mixing apparatus is withdrawn and recirculated by a recirculation loop as shown and described in the Figure of copending application Ser. No. 08/370,694 (Thomas A. DesMarais), filed Jan. 10, 1995, (herein incorporated by reference) to the entry point of the oil and water phase flow streams to the dynamic mixing zone.

The combined mixing and recirculation apparatus is filled with oil phase and water phase at a ratio of 3 parts water to 1 part oil. The dynamic mixing apparatus is vented to allow air to escape while filling the apparatus completely. The flow rates during filling are 3.78 g/sec oil phase and 11.35 cc/sec water phase with about 15 cc/sec in the recirculation loop.

Once the apparatus set-up is filled, the water phase flow rate is cut in half to reduce the pressure build up while the vent is closed. Agitation is then begun in the dynamic mixer, with the impeller turning at 1800 RPM. The flow rate of the water phase is then steadily increased to a rate of 45.4 cc/sec over a time period of about 1 min., and the oil phase flow rate is reduced to 0.757 g/sec over a time period of about 2 min. The recirculation rate is steadily increased to about 45 cc/sec during the latter time period. The back pressure created by the dynamic and static mixers at this point is about 10 PSI (69 kPa). The Waukesha pump speed is then steadily decreased to a yield a recirculation rate of about 11 cc/sec.

B) Polymerization/Curing of HIPE

The formed emulsion flowing from the static mixer at this point is collected in a round polypropylene tub, 17 in. (43 cm) in diameter and 7.5 in (10 cm) high, with a concentric insert made of Celcon plastic. The insert is 5 in (12.7 cm) in diameter at its base and 4.75 in (12 cm) in diameter at its top and is 6.75 in (17.14 cm) high. The emulsion-containing tubs are kept in a room maintained at 65° C. for 18 hours to bring about polymerization of the emulsion in the containers to thereby form polymeric foam.

C) Foam Washing and Dewatering

The cured HIPE foam is removed from the tubs. The foam at this point has residual water phase (containing dissolved emulsifiers, electrolyte, initiator residues, and initiator) about 50–60 times (50–60X) the weight of polymerized monomers. The foam is sliced with a sharp reciprocating saw blade into sheets which are 0.160 inches (0.406 cm) in thickness. These sheets are then subjected to compression in a series of 2 porous nip rolls equipped with vacuum which gradually reduce the residual water phase content of the foam to about 6 times (6X) the weight of the polymerized material. At this point, the sheets are then resaturated with a 1.5% $CaCl_2$ solution at 60° C., are squeezed in a series of 3 porous nip rolls equipped with vacuum to a water phase content of about 4X. The $CaCl_2$ content of the foam is between 8 and 10%.

The foam remains compressed after the final nip at a thickness of about 0.021 in. (0.053 cm). The foam is then dried in air for about 16 hours. Such drying reduces the moisture content to about 9–17% by weight of polymerized material. At this point, the foam sheets are very drapeable. The foam also contains about 5% by weight of residual diglycerol monooleate emulsifier. In the collapsed state, the density of the foam is about 0.14 g/cc. When expanded in Jayco synthetic urine, its free absorbent capacity is about 60 mL/g and has a glass transition temperature of about 23° C.

EXAMPLE 3

Preparation of HIPE Foams from Different Monomers

Absorbent foams are prepared from HIPEs having varying monomer components are prepared using procedures similar to those described in Examples 1 or 2 above. The monomer formulations, water-to-oil (W:O) ratios, and physical properties of these foams (RTCD, Expansion Factor and Tg) are shown in Table 1 below:

TABLE 1

| Sample | Formulation STY:EST:DVB:EHA: DA* | Second Crosslinker Type (DA)* | W:O Ratio** | RTCD (%) | Expansion Factor (X) | Tg (°C.)*** |
|---|---|---|---|---|---|---|
| 1 | 16:7.2:8.8:55:13* | BDMA | 60.7 | 11.5 | 8.3 | 35 |
| 2 | 11.25:13.75:60.5** | EGDMA | 55.8 | 8.0 | 6.5 | 27 |
| 3 | 7:9.9:12.1:63.8 | BDMA | 55.9 | 9.5 | 7.5 | 18 |
| 4 | 10:11.25:13.75:55:10 | HDDA | 62.6 | 5.8 | 6.5 | 31 |
| 5 | 0:21:14:55:10 | HDDA | 60.6 | 6.7 | 6.8 | 22 |
| 6 | 0:21:14:55:10 | HDDA | 59.6 | 8.8 | 7.4 | 23 |
| 7 | 9.5:11.5:14:55:10 | HDDA | 59.8 | 6.3 | 7.7 | 28 |
| 8 | 0:14.4:17.6:68:0 |  | 55.9 | 11.1 | 7.4 |  |

*STY = styrene
EST = ethyl styrene
DVB = divinyl benzene
EHA = 2-ethylhexyl acrylate
BDMA = 1,4-butanediol dimethacrylate.
EGDMA = ethylene glycol dimethacrylate.
HDDA = 1,6-hexanediol diacrylate.
**volume to weight
***by DMA

EXAMPLE 4

Diaper Made with HIPE Foam

A disposable diaper is prepared using the configuration and components shown in expanded and blown-apart depiction in FIG. 7. Such a diaper comprises a topsheet 70, a fluid-impervious backsheet 71, and a dual layer absorbent core positioned between the topsheet and the backing sheet. The dual layer absorbent core comprises a modified hourglass-shaped, fluid storage/redistribution layer 72 comprising the collapsed HIPE foams according to Examples 1, 2 or 3 positioned below a modified-hourglass shaped fluid acquisition layer 73. About 10 grams of this collapsed HIPE foam is used to form this storage/distribution layer 72 which has a surface area of about 52.5 in$^2$ (339 cm$^2$) and a thickness of about 0.1 in (0.25 cm) in its collapsed state.

Topsheet 70 contains two substantially parallel barrier leg cuff strips 74 with elastic. Affixed to the diaper backsheet 71 are two rectangular elasticized waistband members 75. Also affixed to each end of backsheet are two waistshield elements 76 constructed of polyethylene. Also affixed to the backsheet are two parallel leg elastic strips 77. A sheet of polyethylene 78 is affixed to the outside of the backsheet as a dedicated fastening surface for two pieces 79 of Y-tape which can be used to fasten the diaper around the wearer.

The acquisition layer 73 of the diaper core can comprise a 92%/8% wet-laid mixture of stiffened, twisted, curled cellulosic fibers and conventional non-stiffened cellulosic fibers. The stiffened, twisted, curled cellulosic fibers are made from southern softwood kraft pulp (Foley fluff) which has been crosslinked with glutaraldehyde to the extent of about 2.5 mole percent on a dry fiber cellulose anhydroglucose basis. The fibers are crosslinked according to the "dry crosslinking process" as described in U.S. Pat. No. 4,822,453 (Dean et al), issued Apr. 18, 1989.

These stiffened fibers are similar to the fibers having the characteristics described as follows in Table 2:

TABLE 2

| Stiffened, Twisted, Curled Cellulose (STCC) Fibers | |
|---|---|
| Type = | Southern softwood kraft pulp crosslinked with glutaraldehyde to the extent of 1.41 mole percent on a dry fiber cellulose anhydroglucose basis |
| Twist Count Dry = | 6.8 nodes/mm |
| Twist Count Wet = | 5.1 nodes/m |
| 2-Propanol Rentention Value = | 24% |
| Water Retention Value = | 37% |
| Curl Factor = | 0.63 |

The conventional non-stiffened cellulose fibers used in combination with the STCC fibers are also made from Foley fluff. These non-stiffened cellulose fibers are refined to about 200 CSF (Canadian Standard Freeness).

The acquisition layer 73 has an average dry density of about 0.01 g/cm$^3$, an average density upon saturation with synthetic urine, dry weight basis, of about 0.08 g/cm$^3$, and an average basis weight of about 0.03 g/cm$^2$. About 8 grams of the fluid acquisition layer are used in the diaper core. The surface area of the acquisition layer is about 46.8 in$^2$ (302 cm$^2$). It has a thickness of about 0.44 cm. Similar results can be obtained if air-laid stiffened fibers are substituted for the wet-laid stiffened fibers in acquisition layer 73 of the absorbent core. Acquisition layer 73 can also comprise an acquisition/distribution foam made according to Examples 1, 2 or 3 of copending U.S. application Ser. No. 08/370,695 (Keith J. Stone et al), filed Jan. 10, 1995, which is incorporated by reference.

What is claimed is:

1. A process for the preparation of an absorbent polymeric foam material which comprises the steps of:
    A) forming a water-in-oil emulsion from:
        1) an oil phase comprising:
            a) from about 85 to about 98% by weight of a monomer component capable of forming a copolymer having a Tg value of below about 35° C. or lower, the monomer component comprising:
                i) from about 45 to about 70% by weight of a substantially water-insoluble, monofunctional monomer capable of forming a polymer having a Tg of about 25° C. or less;
                ii) from about 10 to about 30% by weight of a substantially water-insoluble, monofunctional comonomer capable of imparting toughness about equivalent to that provided by styrene;

iii) from about 5 to about 25% by weight of a first substantially water-insoluble, polyfunctional crosslinking agent selected from the group consisting of divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; and iv) from 0 to about 15% by weight of a second substantially water-insoluble, polyfunctional crosslinking agent selected from group consisting of polyfunctional acrylates, methacrylates, acrylamides, methacrylamides, and mixtures thereof; and b) from about 2 to about 15% by weight of an emulsifier component which is soluble in the oil phase and which is suitable for forming a stable water-in-oil emulsion, said emulsifier component comprising a primary emulsifier having at least about 40% by weight emulsifying components selected from the group consisting of diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, and linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and 2) a water phase comprising an aqueous solution containing: (a) from about 0.2 to about 20% by weight of a water-soluble electrolyte; and (b) an effective amount of a polymerization initiator;

3) a volume to weight ratio of water phase to oil phase in the range of from about 55:1 to about 100:1; and B) polymerizing the monomer component in the oil phase of the water-in-oil emulsion to form a polymeric foam material.

2. The process of claim 1 comprising the further step of dewatering the polymeric foam material of step B) to an extent such that a collapsed, polymeric foam material is formed that will re-expand upon contact with aqueous fluids.

3. The process of claim 2 wherein the volume to weight ratio of water phase to oil phase is in the range of from about 55:1 to about 75:1.

4. The process of claim 3 wherein the volume to weight ratio of water phase to oil phase is in the range of from about 55:1 to about 65:1.

5. The process of claim 2 wherein:

1) the oil phase comprises:

a) from about 90 to about 97% by weight of a monomer component capable of forming a copolymer having a Tg value from about 15° to about 30° C., said monomer component comprising:

i) from about 50 to about 65% by weight monomer selected from the group consisting of $C_4$–$C_{14}$ alkyl acrylates, aryl acrylates, $C_6$–$C_{16}$ alkyl methacrylates, acrylamides, $C_4$–$C_{12}$ alkyl styrenes and mixtures thereof;

ii) from about 15 to about 23% by weight comonomer selected from the group consisting of styrene, ethyl styrene and mixtures thereof;

iii) from about 12 to about 18% by weight divinyl benzene; and iv) from 7 to about 13% by weight of said second crosslinking agent selected from the group consisting of 1,4-butanediol dimethacrylate, ethylene glycol dimethacrylate, 1,6-hexanediol diacrylate, and mixtures thereof;

b) from about 3 to about 10% by weight of said emulsifier component; and 2) the water phase comprises from about 1 to about 10% calcium chloride.

6. The process of claim 5 wherein monomer (i) is selected from the group consisting of butyl acrylate, hexyl acrylate, octyl acrylate, 2-ethylhexyl acrylate, nonyl acrylate, decyl acrylate, dodecyl acrylate, isodecyl acrylate, tetradecyl acrylate, benzyl acrylate, nonylphenyl acrylate, hexyl methacrylate, octyl methacrylate, nonyl methacrylate, decyl methacrylate, isodecyl methacrylate, dodecyl methacrylate, tetradecyl methacrylate, N-octadecyl acrylamide, p-n-octylstyrene, and mixtures thereof.

7. The process of claim 2 wherein the primary emulsifier comprises emulsifying components selected from the group consisting of diglycerol monooleate, diglycerol monomyristate, diglycerol monoisostearate, diglycerol monoesters of coconut fatty acids, sorbitan monooleate, sorbitan monomyristate, sorbitan monoesters of coconut fatty acids, and mixtures thereof.

8. The process of claim 7 wherein said primary emulsifier comprises at least about 70% by weight of said emulsifying components.

9. The process of claim 2 wherein the emulsifier component further comprises a secondary emulsifier selected from the group consisting of phosphatidyl cholines and phosphatidyl choline-containing compositions, aliphatic betaines, long chain $C_{12}$–$C_{22}$ dialiphatic, short chain $C_1$–$C_4$ dialiphatic quaternary ammonium salts, long chain $C_{12}$–$C_{22}$ dialkoyl(alkenoyl)-2-hydroxyethyl, short chain $C_1$–$C_4$ dialiphatic quaternary ammonium salts, long chain $C_{12}$–$C_{22}$ dialiphatic imidazolinium quaternary ammonium salts, short chain $C_1$–$C_4$ dialiphatic, long chain $C_{12}$–$C_{22}$ monoaliphatic benzyl quaternary ammonium salts, the long chain $C_{12}$–$C_{22}$ dialkoyl(alkenoyl)-2-aminoethyl, short chain $C_1$–$C_4$ monoaliphatic, short chain $C_1$–$C_4$ monohydroxyaliphatic quaternary ammonium salts, and mixtures thereof, at a weight ratio of primary emulsifier to secondary emulsifier of from about 50:1 to about 1:4.

10. The process of claim 8 wherein the secondary emulsifier is selected from the group consisting of ditallow dimethyl ammonium chloride, ditallow dimethyl ammonium methylsulfate, and mixtures thereof and wherein the weight ratio of primary to secondary emulsifier is from about 30:1 to about 2:1.

* * * * *

UNITED STATES PATENT AND TRADEMARK OFFICE
CERTIFICATE OF CORRECTION

PATENT NO. : 5,744,506
DATED : April 28, 1998
INVENTOR(S) : Stephen Allen Goldman, et. al.

It is certified that error appears in the above-identified patent and that said Letters Patent is hereby corrected as shown below:

Title page, item [54] and col. 2, in the Title, "FORAM" should read -- FOAM --; and "AQUEAOUS" should read --AQUEOUS--.

Column 4, line 14, "steps of" should read -- steps of: --.

Column 10, line 31, "of s the" should read -- of the --.

Column 14, line 12, "mires" should read -- mixtures --.

Column 14, line 31, "thereof" should read -- thereof. --.

Column 14, line 40, "catechol" should read -- catechol, --.

Column 14, line 41, "resorcinol" should read -- resorcinol, --.

Column 21, line 12, "HIE" should read -- HIPE --.

Column 22, line 20, "absorbent s foam" should read -- absorbent foam --.

Signed and Sealed this

Fourteenth Day of December, 1999

Attest:

Q. TODD DICKINSON

*Attesting Officer*  *Acting Commissioner of Patents and Trademarks*